United States Patent
Lange et al.

(10) Patent No.: US 12,016,944 B2
(45) Date of Patent: Jun. 25, 2024

(54) MIXTURES COMPRISING A PROTEIN EXTRACT FOR THE TREATMENT OF HUMAN SKIN AND/OR HAIR

(71) Applicant: Symrise AG, Holzminden (DE)

(72) Inventors: Sabine Lange, Holzminden (DE); Martina Herrmann, Hameln (DE); Dominik Stuhlmann, Holzminden (DE); Ann-Christin Weseloh, Polle (DE); Adelino Nakano, Indaiatuba (BR); Carolina Lourenço, Cotia (BR)

(73) Assignee: Symrise AG, Holzminden (DE)

( * ) Notice: Subject to any disclaimer, the term of this patent is extended or adjusted under 35 U.S.C. 154(b) by 16 days.

(21) Appl. No.: 16/977,989

(22) PCT Filed: Mar. 8, 2018

(86) PCT No.: PCT/EP2018/055758
§ 371 (c)(1),
(2) Date: Sep. 3, 2020

(87) PCT Pub. No.: WO2019/170238
PCT Pub. Date: Sep. 12, 2019

(65) Prior Publication Data
US 2021/0069086 A1    Mar. 11, 2021

(51) Int. Cl.
| | | |
|---|---|---|
| *A61K 8/64* | (2006.01) |
| *A61K 8/34* | (2006.01) |
| *A61K 8/362* | (2006.01) |
| *A61K 8/365* | (2006.01) |
| *A61K 8/891* | (2006.01) |
| *A61Q 5/00* | (2006.01) |
| *A61Q 5/02* | (2006.01) |
| *A61Q 5/12* | (2006.01) |
| *A61Q 17/04* | (2006.01) |
| *A61Q 19/00* | (2006.01) |

(52) U.S. Cl.
CPC ............... *A61K 8/645* (2013.01); *A61K 8/34* (2013.01); *A61K 8/345* (2013.01); *A61K 8/362* (2013.01); *A61K 8/365* (2013.01); *A61K 8/891* (2013.01); *A61Q 5/002* (2013.01); *A61Q 5/02* (2013.01); *A61Q 5/12* (2013.01); *A61Q 17/04* (2013.01); *A61Q 19/00* (2013.01)

(58) Field of Classification Search
CPC ........ A61K 8/345; A61K 8/362; A61Q 5/002; A61Q 5/02
See application file for complete search history.

(56) References Cited

U.S. PATENT DOCUMENTS

| | | | | |
|---|---|---|---|---|
| 3,996,146 A * | 12/1976 | Tarasov | ................... | A61Q 5/02 510/495 |
| 6,063,367 A * | 5/2000 | Manzo | ..................... | A61Q 5/00 424/70.14 |
| 6,468,549 B1 * | 10/2002 | Dupuis | ................... | A61K 8/365 424/59 |
| 2009/0069439 A1 * | 3/2009 | Pertile | ..................... | A61P 17/14 435/375 |

FOREIGN PATENT DOCUMENTS

| | | |
|---|---|---|
| EP | 0 862 907 A2 | 9/1998 |
| EP | 2 772 245 A1 | 9/2014 |
| WO | 90/05521 A1 | 5/1990 |
| WO | 2013/062782 A1 | 5/2013 |

\* cited by examiner

*Primary Examiner* — Andrew S Rosenthal
(74) *Attorney, Agent, or Firm* — Dilworth & Barrese, LLP

(57) ABSTRACT

Suggested is a mixture comprising or consisting of: (a) a protein extract obtained from cereal gluten extracted by means of aqueous ethanol, said extract being characterized by a content of at least 50 wt.-% proteins having a molecular weight of at least 22 kDa; (b) at least one organic acid; and (c) at least one cosmetically acceptable carrier.

13 Claims, 3 Drawing Sheets

MIXTURES COMPRISING A PROTEIN EXTRACT FOR THE TREATMENT OF HUMAN SKIN AND/OR HAIR

FIELD OF INVENTION

The present invention belongs to the area of hair care products and refers to a mixture comprising certain protein extracts and conditioning agents for protecting human hair and improving certain properties of so-called two-in-one shampoos.

STATE OF THE ART

During the life cycle of a human hair, the hair structure changes, particularly as a result of mechanical stress, e.g. by combing or back-combing, or else as a result of chemical treatment, for example bleaching, colouring or perming. Particularly damage impairs the surface properties of the hair, e.g. as regards gloss, suppleness or combability and generally reduces its strength. Damaged hair breaks more easily than undamaged hair.

It has been known for some time that protein hydrolysates, which can be prepared by degradation of native proteins, have hair care properties. These hydrolysates chiefly contain peptides having a molecular weight in the range from 2-3 kDa and can be obtained from various protein sources, for example from cereal gluten by degreasing the gluten and then extracting it under alkaline conditions.

RELEVANT PATENT DOCUMENTS

As an example, the commonly assigned WO 1990 05521 A1 describes a hydrolysate which is obtained from cereal gluten, preferably wheat gluten, in a multi-stage process, and which can be used, inter alia, in hair care products. According to this specification, the dried gluten is firstly degreased using a fat solvent and then extracted using aqueous ethanol which has been rendered alkaline using ammonia. The extraction residue is discarded, and the liquid phase is cooled, if necessary under full vacuum, during which a protein product is precipitated out which, after being separated off, forms a clear hydrolysate composition which, at room temperature, resembles honey. This composition can be conditioned and further processed for the desired purposes.

Hydrolysates of this type are absorbed by the hair relatively uniformly and are to be found not only in the outer cell layer of scales (cuticula) of the hair, but also in the region of the fibrous shaft (cortex). Such behaviour is very desirable for the more preventive care of still largely undamaged hair.

For hair which is already more severely damaged, EP 0862907 B1 (SYMRISE) suggests specific protein extracts different from conventional protein hydrolysate, essentially consisting of the native cereal proteins (prolamines) (in the case of wheat therefore gliadin), which are virtually insoluble in water, compared with the hydrolysates, and whose main fraction has a molecular weight of 28-39 kDa. Different from hydrolysates, these extracts do not coat the hair with a uniform film and do not diffuse into deeper regions of the hair either, but binds primarily to damaged sites in human hair, particularly to split ends or to sections of hair damaged by combing or back-combing.

Notwithstanding these facts there is still a need for intelligent hair care actives providing improved performance for example in terms of easier combability to prevent damaging and to repair and protect keratin fibres against mechanical stress, chemical stress and environmental pollution.

Proteins are also known to be beneficial for skin care. Within cosmetic formulations they are valued for their strong moisturizing and film forming properties. When applied topically, protein has the unique ability to bind and hold water in the skin. Similar to a humectant, the ability to hold water improves the appearance of aged skin by providing hydration and assisting barrier repair.

Therefore, it has been a first object of the present invention providing hair care actives with improved properties, particularly based on protein extracts which have already been found to be excellent in the treatment of damaged hair.

Another object of the present invention has been improving water-resistance of such compositions, particularly of formulations comprising primary or secondary sun protection filters, regardless whether these products are designated for application on hair or skin.

DESCRIPTION OF THE INVENTION

The object of the present invention is directed to a mixture comprising or consisting of:
  (a) a protein extract obtained from cereal gluten extracted by means of aqueous ethanol, said extract being characterized by a content of at least 50 wt.-% proteins having a molecular weight of at least 22 kDa;
  (b) at least one organic acid; and
  (c) at least one cosmetically acceptable carrier.

Surprisingly, it has been observed that the specific protein extract composition—titled as "SymHair® Restore"—has capability to coat and to penetrate into such fibers, show serious improvements in terms of tensile strength, split ends repair, swelling, break resistance and in particular combability. The latter is of specific importance, since this feature is not specifically related to damaged hair, but also to keratin fibers which have not been exposed to specific stress like bleaching, permanent waving and the like.

BRIEF DESCRIPTION OF THE DRAWINGS

The present invention will be described in greater detail with reference to the accompanying drawings, in which.

DESCRIPTION OF THE PREFERRED EMBODIMENTS

Protein Extracts

Figure 1:
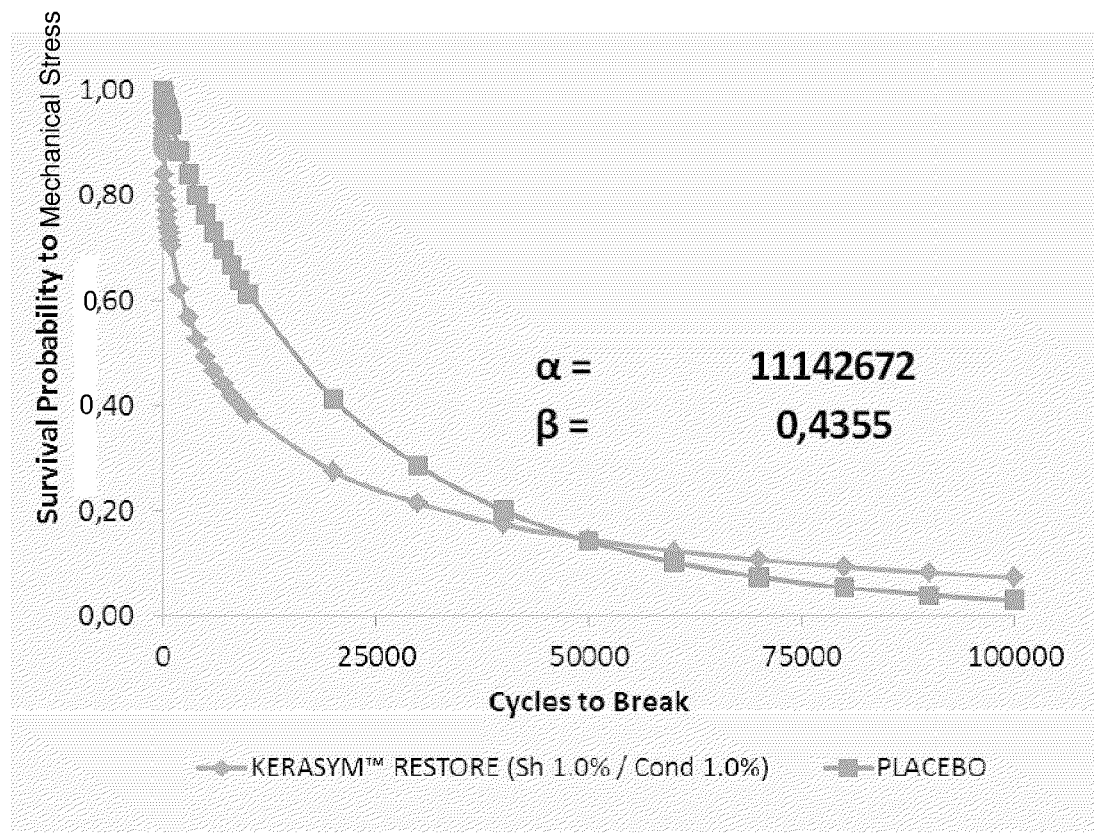
FIG. 1 is a graph illustrating performance of the present invention.

Protein extracts (compound a) are basically known from the state of the art as indicated above. The specific extracts according to the present invention are obtained in the form of an alcoholic extraction solution from dried cereal gluten, preferably wheat gluten, which solution has been treated with glycerol and/or a short-chain alkanediol and evaporated under reduced pressure until the alcohol content is less than 5 percent by weight, preferably less than 1 percent by weight.

More particularly the extracts are obtained according to the following protocol:
  (i) extracting dried cereal gluten under neutral conditions with an extraction medium comprising dilute alkanol so as to obtain a liquid extract comprising proteins, wherein the protein fraction of the extract consists essentially of prolamines;
  (Ii) removing solid residue from the resulting liquid extract so as to produce a liquid phase;
  (iii) treating said liquid phase with a polyhydric alcohol selected from the group consisting of glycerol and a short chain alkanediol; and
  (iv) concentrating the resultant treated liquid phase under reduced pressure until the resultant liquid concentrate has an alkanol content of less than 5 percent by weight.

A particularly advantageous protein extract is one which has been prepared by extracting the dried cereal gluten, preferably wheat gluten, using dilute short-chain alkanol, preferably ethanol, treating the liquid phase, following removal of the solid residue, with glycerol or, when required, a short-chain alkanediol, such as, for example, ethylene glycol or propylene glycol, and evaporating it under reduced pressure until the content of alkanol in the liquid phase has decreased to less than 5 percent by weight, preferably less than 1 percent by weight. Extraction is preferably carried out with 50-90 percent, preferably 60-70 percent, ethanol as extractant, the ratio of gluten to extractant being from 1:15 to 1:2, preferably 1:10 to 1:5, and at temperatures of 15 to 45° C., preferably at 20 to 30° C. The extraction time can be 0.25 to 48 hours and is normally in the region of 1 to 4 hours, depending on the equipment used. The protein content in the evaporated extract is 1 to 30% of protein, preferably 10% b.w. of protein.

Organic Acids

Suitable organic acids (component b) can be selected from the group consisting of citric acid, lactic acid, isocitric acid, tartaric acid, malic acid, glycolic acid, mandelic acid, tartronic acid and their mixtures.

Carriers

The mixtures according to the present inventions incorporate carriers (component c) or—as a synonym—solvents which may be selected from the group consisting of water, $C_1$-$C_4$ aliphatic alcohols, alkylene glycols, glycerol and their mixtures. Suitable alcohols encompass ethanol, propanol, isopropyl alcohol and the isomers of butanol. Suitable polyols preferably contain 2 to 15 carbon atoms and at least two hydroxyl groups. The polyols may contain other functional groups, more especially amino groups, or may be modified with nitrogen. Typical examples are
  glycerol;
  alkylene glycols such as, for example, ethylene glycol, diethylene glycol, propylene glycol, butylene glycol, hexylene glycol and polyethylene glycols with an average molecular weight of 100 to 1000 Dalton;
  technical oligoglycerol mixtures with a degree of self-condensation of 1.5 to 10, such as for example technical diglycerol mixtures with a diglycerol content of 40 to 50% by weight;
  methylol compounds such as, in particular, trimethylol ethane, trimethylol propane, trimethylol butane, pentaerythritol and dipentaerythritol;
  lower alkyl glucosides, particularly those containing 1 to 8 carbon atoms in the alkyl group, for example methyl and butyl glucoside;
  sugar alcohols containing 5 to 12 carbon atoms, for example sorbitol or mannitol,
  sugars containing 5 to 12 carbon atoms, for example glucose or sucrose;
  amino sugars, for example glucamine;
  dialcoholamines, such as diethanolamine or 2-aminopropane-1,3-diol.

The mixtures may comprise these carriers or solvents in amounts of about 50 to about 99. % b.w., preferably about 60 to about 90% b.w. and more preferably about 70 to about 80% b.w.

In a preferred embodiment the mixtures according to the present invention may comprise or consist of:
  (a) about 5 to about 15 wt.-%, preferably about 9 to about 11 w.-% protein extract; and
  (b) about 0.01 to about 2.0 wt.-%, preferably about 0.03 to about 0.1 wt.-% organic acids;
  (c) on condition that the amount add with said carriers and optionally further additives—such as for example condition agents—to 100 wt.-%.

Conditioning Agents

The mixtures according to the present invention may incorporate also at least one hair conditioning agent. In the context of the present invention a conditioning agent (compound d) is a compound capable of coating on the surface and/or penetrating into a keratin fibre when applied to human hair. Typical examples encompass quaternary surfactants, cationic polymers and silicones and binary and ternary mixtures of these compounds.

Cationic Surfactants

Tetraalkyl ammonium salts. Cationically active surfactants comprise the hydrophobic high molecular group required for the surface activity in the cation by dissociation in aqueous solution. A group of important representatives of the cationic surfactants are the tetraalkyl ammonium salts of the general formula: $(R^1R^2R^3R^4N^+)X^-$. Here R1 stands for $C_1$-$C_8$ alk(en)yl, $R^2$, $R^3$ and $R^4$, independently of each other, for alk(en)yl radicals having 1 to 22 carbon atoms. X is a counter ion, preferably selected from the group of the halides, alkyl sulfates and alkyl carbonates. Cationic surfactants, in which the nitrogen group is substituted with two long acyl groups and two short alk(en)yl groups, are particularly preferred.

Esterquats. A further class of cationic surfactants particularly useful as co-surfactants for the present invention is represented by the so-called esterquats. Esterquats are generally understood to be quaternised fatty acid triethanolamine ester salts. These are known compounds which can be obtained by the relevant methods of preparative organic chemistry. Reference is made in this connection to International patent application WO 91/01295 A1, according to which triethanolamine is partly esterified with fatty acids in the presence of hypophosphorous acid, air is passed through the reaction mixture and the whole is then quaternised with dimethyl sulphate or ethylene oxide. In addition, German patent DE 4308794 C1 describes a process for the production of solid esterquats in which the quaternisation of triethanolamine esters is carried out in the presence of suitable dispersants, preferably fatty alcohols.

Typical examples of esterquats suitable for use in accordance with the invention are products of which the acyl component derives from monocarboxylic acids corresponding to formula RCOOH in which RCO is an acyl group containing 6 to 10 carbon atoms, and the amine component is triethanolamine (TEA). Examples of such monocarboxylic acids are caproic acid, caprylic acid, capric acid and technical mixtures thereof such as, for example, so-called head-fractionated fatty acid. Esterquats of which the acyl component derives from monocarboxylic acids containing 8 to 10 carbon atoms, are preferably used. Other esterquats are those of which the acyl component derives from dicarboxylic acids like malonic acid, succinic acid, maleic acid, fumaric acid, glutaric acid, sorbic acid, pimelic acid, azelaic acid, sebacic acid and/or dodecanedioic acid, but preferably adipic acid. Overall, esterquats of which the acyl component derives from mixtures of monocarboxylic acids containing 6 to 22 carbon atoms, and adipic acid are preferably used. The molar ratio of mono and dicarboxylic acids in the final esterquat may be in the range from 1:99 to 99:1 and is preferably in the range from 50:50 to 90:10 and more particularly in the range from 70:30 to 80:20. Besides the quaternised fatty acid triethanolamine ester salts, other suitable esterquats are quaternized ester salts of mono-/dicarboxylic acid mixtures with diethanolalkyamines or 1,2-dihydroxypropyl dialkylamines. The esterquats may be obtained both from fatty acids and from the corresponding triglycerides in admixture with the corresponding dicarboxylic acids. One such process, which is intended to be representative of the relevant prior art, is proposed in European patent EP 0750606 B1. To produce the quaternised esters, the mixtures of mono- and dicarboxylic acids and the triethanolamine—based on the available carboxy) functions—may be used in a molar ratio of 1.1:1 to 3:1. With the performance properties of the esterquats in mind, a ratio of 1.2:1 to 2.2:1 and preferably 1.5:1 to 1.9:1 has proved to be particularly advantageous. The preferred esterquats are technical mixtures of mono-, di- and triesters with an average degree of esterification of 1.5 to 1.9.

Cationic Polymers and Silicones

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, amodimethicone, copolymers of adipic acid and dimethylaminohydroxypropyl diethylenetriamine (Cartaretine®, Sandoz), copolymers of acrylic acid with dimethyl diallyl ammonium chloride (Merquat® 550, Chemviron), polyaminopolyamides and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bisdimethylamino-1,3-propane, cationic guar gum such as, for example, Jaguar®CBS, Jaguar®C-17, Jaguar®C-16 of Celanese, quaternized ammonium salt polymers such as, for example, Mirapol® A-15, Mirapol® AD-1, Mirapol® AZ-1 of Miranol and the various polyquaternium types (for example 6, 7, 32 or 37) which can be found in the market under the tradenames Rheocare® CC or Ultragel® 300.

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates. A detailed overview of suitable volatile silicones can be found in Todd et al. in Cosm. Toil. 91, 27 (1976).

Cosmetic and Personal Care Compositions

Another object of the present invention encompasses cosmetic or personal care compositions such as for example a skin care, hair care and/or sun care product, preferably a cosmetic cream, lotion, spray, emulsion, ointment, gel or mouse an the like. Typical examples are skin creams and hair shampoos, antiperspirants and soaps.

A particularly preferred hair care composition may be a shampoo or a conditioner, preferably is represents a so called "two-in-one" shampoo, which means a shampoo that simultaneously acts as a conditioner. Such product may represent a rinse-off or leave-on composition, comprising said mixture of compounds (a), (b) and (c) in an amount of from about 0.1 to about 10% b.w., preferably about 0.5 to 5% b.w. and more preferably about 1 to about 2% b.w.—calculated on the total composition.

More particularly, the compositions may comprise the mixtures encompassing components (a), (b) and (c) in an amount of from about 0.5 to about 5% b.w. and preferably in an amount of from 1% to about 2% b.w.

To avoid any ambiguity the term "% b.w." has the meaning of percent by weight.

The preparations according to the invention may contain abrasives, anti-acne agents, agents against ageing of the skin, anti-cellulitis agents, antidandruff agents, anti-inflammatory agents, irritation-preventing agents, irritation-inhibiting agents, antioxidants, astringents, perspiration-inhibiting agents, antiseptic agents, ant-statics, binders, buffers, carrier materials, chelating agents, cell stimulants, cleansing agents, care agents, depilatory agents, surface-active substances, deodorizing agents, antiperspirants, softeners, emulsifiers, enzymes, essential oils, fibres, film-forming agents, fixatives, foam-forming agents, foam stabilizers, substances for preventing foaming, foam boosters, gelling agents, gel-forming agents, hair care agents, hair-setting agents, hair-straightening agents, moisture-donating agents, moisturizing substances, moisture-retaining substances, bleaching agents, strengthening agents, stain-removing agents, optically brightening agents, impregnating agents, dirt-repellent agents, friction-reducing agents, lubricants, moisturizing creams, ointments, opacifying agents, plasticizing agents, covering agents, polish, gloss agents, polymers, powders, proteins, re-oiling agents, abrading agents, silicones, skin-soothing agents, skin-cleansing agents, skin care agents, skin-healing agents, skin-lightening agents, skin-protecting agents, skin-softening agents, hair promotion agents, cooling agents, skin-cooling agents, warming agents, skin-warming agents, stabilizers, UV-absorbing agents, UV filters, detergents, fabric conditioning agents, suspending agents, skin-tanning agents, thickeners, vitamins, oils, waxes, fats, phospholipids, saturated fatty acids, mono- or polyunsaturated fatty acids, α-hydroxy acids, polyhydroxyfatty acids, liquefiers, dyestuffs, colour-protecting agents, pigments, anti-corrosives, aromas, flavouring substances, odoriferous substances, polyols, surfactants, electrolytes, organic solvents or silicone derivatives and the like as additional auxiliaries and additives.

Surfactants

Preferred auxiliaries and additives are anionic and/or amphoteric or zwitterionic surfactants. Typical examples of anionic surfactants are soaps, alkyl benzenesulfonates, alkanesulfonates, olefin sulfonates, alkylether sulfonates, glycerol ether sulfonates, methyl ester sulfonates, sulfofatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution. Typical examples of amphoteric or zwitterionic surfactants are alkylbetaines, alkylamidobetaines, aminopropionates, aminoglycinates, imidazolinium betaines and sulfobetaines. The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside and Mineraloladditive (Catalysts, Surfactants and Mineral Oil Additives)", Thieme Verlag, Stuttgart, 1978, pages 123-217. The percentage content of surfactants in the preparations may be from 0.1 to 10% by weight and is preferably from 0.5 to 5% by weight, based on the preparation.

Oil Bodies

Suitable oil bodies, which form constituents of the O/W emulsions, are, for example, Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkylhydroxy carboxylic acids with linear or branched $C_6$-$C_{22}$-fatty alcohols, in particular Dioctyl Malate, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as, for example, Dicaprylyl Carbonate (Cetiol® CC), Guerbet carbonates, based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or asymmetrical dialkyl ethers having 6 to 22 carbon atoms per alkyl group, such as, for example, dicaprylyl ether (Cetiol® OE), ring-opening products of epoxidized fatty acid esters with polyols, silicone oils (cyclomethicones, silicone methicone grades, etc.) and/or aliphatic or naphthenic hydrocarbons, such as, for example, squalane, squalene or dialkylcyclohexanes.

Emulsifiers

Other surfactants may also be added to the preparations as emulsifiers, including for example:

products of the addition of 2 to 30 mol ethylene oxide and/or 0 to 5 mol propylene oxide onto linear $C_{8-22}$ fatty alcohols, onto $C_{12-22}$ fatty acids and onto alkyl phenols containing 8 to 15 carbon atoms in the alkyl group;

$C_{12/18}$ fatty acid monoesters and diesters of addition products of 1 to 30 molethylene oxide onto glycerol;

glycerol mono- and diesters and sorbitan mono- and diesters of saturated and unsaturated fatty acids containing 6 to 22 carbon atoms and ethylene oxide addition products thereof;

addition products of 15 to 60 mol ethylene oxide onto castor oil and/or hydrogenated castor oil;

polyol esters and, in particular, polyglycerol esters such as, for example, polyglycerol polyricinoleate, polyglycerol poly-12-hydroxystearate or polyglycerol dimerate isostearate. Mixtures of compounds from several of these classes are also suitable;

addition products of 2 to 15 mol ethylene oxide onto castor oil and/or hydrogenated castor oil;

partial esters based on linear, branched, unsaturated or saturated $C_{6/22}$ fatty acids, ricinoleic acid and 12-hydroxystearic acid and glycerol, polyglycerol, pentaerythritol, -dipentaerythritol, sugar alcohols (for example sorbitol), alkyl glucosides (for example methyl glucoside, butyl glucoside, lauryl glucoside) and polyglucosides (for example cellulose);

mono-, di and trialkyl phosphates and mono-, di- and/or tri-PEG-alkyl phosphates and salts thereof;

wool wax alcohols;

polysiloxane/polyalkyl polyether copolymers and corresponding derivatives;

mixed esters of pentaerythritol, fatty acids, citric acid and fatty alcohol and/or mixed esters of $C_{6-22}$ fatty acids, methyl glucose and polyols, preferably glycerol or polyglycerol, polyalkylene glycols and glycerol carbonate.

The addition products of ethylene oxide and/or propylene oxide onto fatty alcohols, fatty acids, alkylphenols, glycerol mono- and diesters and sorbitan mono- and diesters of fatty acids or onto castor oil are known commercially available products. They are homologue mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide onto glycerol are known as lipid layer enhancers for cosmetic formulations. The preferred emulsifiers are described in more detail as follows:

Partial glycerides. Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 mol ethylene oxide onto the partial glycerides mentioned are also suitable.

Sorbitan esters. Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable.

Polyglycerol esters. Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 lsostearate (Isolan® GI 34), Polyglyceryl-3 Oleate, Diisostearoyl Polyglyceryl-3 Diisostearate (Isolan® PDI), Polyglyceryl-3 Methylglucose Distearate (Tego Care® 450), Poly-glyceryl-3 Beeswax (Cera Bellinal, Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate lsostearate and mixtures thereof. Examples of other suitable polyolesters are the mono-, di- and triesters of trimethylol propane or pentaerythritol with lauric acid, cocofatty acid, tallow fatty acid, palmitic acid, stearic acid, oleic acid, behenic acid and the like optionally reacted with 1 to 30 mol ethylene oxide.

Anionic emulsifiers. Typical anionic emulsifiers are aliphatic $C_{12-22}$ fatty acids, such as palmitic acid, stearic acid or behenic acid for example, and $C_{12-22}$ dicarboxylic acids, such as azelaic acid or sebacic acid for example.

Amphoteric emulsifiers. Other suitable emulsifiers are amphboteric or zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine.

Superfatting Agents and Consistency Factors

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used.

Thickening Agents and Rheology Additives

Suitable thickeners are polymeric thickeners, such as Aerosil® types (hydrophilic silicas), polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates and electrolytes, such as sodium chloride and ammonium chloride.

Pearlizing Waxes

Suitable pearlising waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxy-substituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

Polymers

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Waxes and Stabilizers

Besides natural oils used, waxes may also be present in the preparations, more especially natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes.

Metal salts of fatty acids such as, for example, magnesium, aluminium and/or zinc stearate or ricinoleate may be used as stabilizers.

Primary Sun Protection Factors

Primary sun protection factors in the context of the invention are, for example, organic substances (light filters) which are liquid or crystalline at room temperature and which are capable of absorbing ultraviolet radiation and of releasing the energy absorbed in the form of longer-wave radiation, for example heat.

The formulations according to the invention advantageously contain at least one UV-A filter and/or at least one UV-B filter and/or a broadband filter and/or at least one inorganic pigment. Formulations according to the invention preferably contain at least one UV-B filter or a broadband filter, more particularly preferably at least one UV-A filter and at least one UV-B filter.

Preferred cosmetic compositions, preferably topical formulations according to the present invention comprise one, two, three or more sun protection factors selected from the group consisting of 4-aminobenzoic acid and derivatives, salicylic acid derivatives, benzophenone derivatives, dibenzoylmethane derivatives, diphenyl acrylates, 3-imidazol-4-yl acrylic acid and esters thereof, benzofuran derivatives, benzylidene malonate derivatives, polymeric UV absorbers containing one or more organosilicon radicals, cinnamic acid derivatives, camphor derivatives, trianilino-s-triazine derivatives, 2-hydroxyphenylbenzotriazole derivatives, phenylbenzimidazole sulfonic acid derivatives and salts thereof, anthranilic acid menthyl esters, benzotriazole derivatives and indole derivatives.

In addition, it is advantageous to combine compounds of formula (I) with active ingredients which penetrate into the skin and protect the skin cells from inside against sun-light-induced damage and reduce the level of cutaneous matrix metalloproteases. Preferred respective ingredients, so called arylhydrocarbon receptor antagonists, are described in WO 2007/128723, incorporated herein by reference. Preferred is 2-benzylidene-5,6-dimethoxy-3,3-dimethylindan-1-one.

The UV filters cited below which can be used within the context of the present invention are preferred but naturally are not limiting.

UV filters which are preferably used are selected from the group consisting of
p-aminobenzoic acid
p-aminobenzoic acid ethyl ester (25 mol) ethoxylated (INCI name: PEG-25 PABA)
p-dimethylaminobenzoic acid-2-ethylhexyl ester
p-aminobenzoic acid ethyl ester (2 mol) N-propoxylated
p-aminobenzoic acid glycerol ester
salicylic acid homomenthyl ester (homosalates) (Neo Heliopan®HMS)
salicylic acid-2-ethylhexyl ester (Neo Heliopan®OS)
triethanolamine salicylate
4-isopropyl benzyl salicylate
anthranilic acid menthyl ester (Neo Heliopan®MA)
diisopropyl cinnamic acid ethyl ester
p-methoxycinnamic acid-2-ethylhexyl ester (Neo Heliopan®AV)
diisopropyl cinnamic acid methyl ester
p-methoxycinnamic acid isoamyl ester (Neo Heliopan®E 1000)
p-methoxycinnamic acid diethanolamine salt
p-methoxycinnamic acid isopropyl ester
2-phenylbenzimidazole sulfonic acid and salts (Neo Heliopan®Hydro)
3-(4'-trimethylammonium) benzylidene bornan-2-one methyl sulfate
beta-imidazole-4(5)-acrylic acid (urocanic acid)
3-(4'-sulfo)benzylidene bornan-2-one and salts
3-(4'-methyl benzylidene)-D,L-camphor (Neo Heliopae-MBC)
3-benzylidene-D,L-camphor
N-[(2 and 4)-[2-(oxoborn-3-ylidene) methyl]benzyl] acrylamide polymer
4,4'-[(6-[4-(1,1-dimethyl)aminocarbonyl) phenylamino]-1,3,5-triazine-2,4-diyl)diimino]-bis-(benzoic acid-2-ethylhexyl ester) (Uvasorb®HEB)
benzylidene malonate polysiloxane (Parsol®SLX)
glyceryl ethylhexanoate dimethoxycinnamate
dipropylene glycol salicylate
tris(2-ethylhexyl)-4,4',4''-(1,3,5-triazine-2,4,6-triyltriimino) tribenzoate(=2,4,6-trianilino-(p-carbo-2'-ethylhexyl-1'-oxy)-1,3,5-triazine) (Uvinul®T150).

Broadband filters which are preferably combined with one or more compounds of formula (I) in a preparation according to the present invention are selected from the group consisting of
2-ethylhexyl-2-cyano-3,3-diphenyl acrylate (Neo Heliopan®303)
ethyl-2-cyano-3,3'-diphenyl acrylate
2-hydroxy-4-methoxybenzophenone (Neo Heliopan®BB)
2-hydroxy-4-methoxybenzophenone-5-sulfonic acid
dihydroxy-4-methoxybenzophenone
2,4-dihydroxybenzophenone
tetrahydroxybenzophenone
2,2'-dihydroxy-4,4'-dimethoxybenzophenone
2-hydroxy-4-n-octoxybenzophenone
2-hydroxy-4-methoxy-4'-methyl benzophenone
sodium hydroxymethoxybenzophenone sulfonate
disodium-2,2'-dihydroxy-4,4'-dimethoxy-5,5'-disulfobenzophenone phenol, 2-(2H-benzotriazol-2-yl)-4-methyl-6-(2-methyl-3 (1,3,3,3-tetramethyl-1-(trimethylsilyl)oxy)disiloxyanyl) propyl) (Mexoryl®XL)

2,2'-methylene bis-(6-(2H-benzotriazol-2-yl)-4-1,1,3,3-tetramethylbutyl) phenol) (Tinosorb® M)

2,4-bis-[4-(2-ethylhexyloxy)-2-hydroxyphenyl]-1,3,5-triazine 2,4-bis-[{(4-(2-ethylhexyloxy)-2-hydroxy}phenyl]-6-(4-methoxyphenyl)-1,3,5-triazine (TinosoreS)

2,4-bis-[{(4-(3-sulfonato)-2-hydroxypropyloxy)-2-hydroxy}phenyl]-6-(4-methoxyphenyl)-1,3,5-triazine sodium salt 2,4-bis-[{(3-(2-propyloxy)-2-hydroxypropyloxy)-2-hydroxy}phenyl]-6-(4-methoxyphenyl)-1,3,5-triazine 2,4-bis-[{4-(2-ethylhexyloxy)-2-hydroxy}phenyl]-6-[4-(2-methoxyethyl carbonyl) phenylamino]-1,3,5-triazine 2,4-bis-[{4-(3-(2-propyloxy)-2-hydroxypropyloxy)-2-hydroxy}phenyl]-6-[4-(2-ethylcarboxyl) phenylamino]-1,3,5-triazine 2,4-bis-[{4-(2-ethylhexyloxy)-2-hydroxy}phenyl]-6-(1-methylpyrrol-2-yl)-1,3,5-triazine 2,4-bis-[{4-tris-(trimethylsiloxysilylpropyloxy)-2-hydroxy}phenyl]-6-(4-methoxyphenyl)-1,3,5-triazine 2,4-bis-[{4-(2"-methylpropenyloxy)-2-hydroxy}phenyl]-6-(4-methoxyphenyl)-1,3,5-triazine 2,4-bis-[{4-(1',1',1',3',5',5',5'-heptamethylsiloxy-2"-methyl-propyloxy)-2-hydroxy}phenyl]-6-(4-methoxyphenyl)-1,3,5-triazine.

The compositions can comprise further typical detergent and cleansing composition ingredients such as UV-A filters filters which are preferably combined with one or more compounds of formula (I) in a preparation according to the present invention are selected from the group consisting of 4-isopropyl dibenzoyl methane terephthalylidene dibornane sulfonic acid and salts (MexoryrSX)

4-t-butyl-4'-methoxydibenzoyl methane (avobenzone)/ (Neo Heliopan® 357)

phenylene bis-benzimidazyl tetrasulfonic acid disodium salt (Neo Heliopan® AP)

2,2'-(1,4-phenylene)-bis-(1H-benzimidazole-4,6-disulfonic acid), monosodium salt 2-(4-diethylamino-2-hydroxybenzoyl) benzoic acid hexyl ester (Uvinul® A Plus)

indanylidene compounds in accordance with DE 100 55 940 A1(=WO 2002 038537 A1)

The compositions can comprise further typical detergent and cleansing composition ingredients such as UV filters which are more preferably combined with one or more compounds of formula (I) in a preparation according to the present invention are selected from the group consisting of p-aminobenzoic acid 3-(4'-trimethylammonium) benzylidene bornan-2-one methyl sulfate salicylic acid homomenthyl ester (Neo Heliopan®HMS)

2-hydroxy-4-methoxybenzophenone (Neo Heliopan®BB)

2-phenylbenzimidazole sulfonic acid (Neo Heliopan®Hydro)

terephthalylidene dibornane sulfonic acid and salts (Mexoryl®SX)

4-tert-butyl-4'-methoxydibenzoyl methane (Neo Heliopan®357)

3-(4'-sulfo)benzylidene bornan-2-one and salts 2-ethylhexyl-2-cyano-3,3-diphenyl acrylate (Neo Heliopan®303)

N-[(2 and 4)-[2-(oxoborn-3-ylidene) methyl]benzyl] acrylamide polymer p-methoxycinnamic acid-2-ethylhexyl ester (Neo Heliopan®AV)

p-aminobenzoic acid ethyl ester (25 mol) ethoxylated (INCI name: PEG-25 PABA)

p-methoxycinnamic acid isoamyl ester (Neo Heliopan®E1000)

2,4,6-trianilino-(p-carbo-2'-ethylhexyl-1'-oxy)-1,3,5-triazine (UvinurT150)

phenol, 2-(2H-benzotriazol-2-yl)-4-methyl-6-(2-methyl-3 (1,3,3,3-tetramethyl-1-(trimethylsilyl)oxy)disiloxyanyl) propyl) (Mexoryl®XL)

4,4'-[(6-[4-(1,1-dimethyl)aminocarbonyl) phenylamino]-1,3,5-triazine-2,4-diyl)diimino]-bis-(benzoic acid-2-ethylhexyl ester) (Uvasorb HEB)

3-(4'-methyl benzylidene)-D,L-camphor (Neo Heliopan®MBC)

3-benzylidene camphor salicylic acid-2-ethylhexyl ester (Neo Heliopan®OS)

4-dimethylaminobenzoic acid-2-ethylhexyl ester (Padimate 0)

hydroxy-4-methoxybenzophenone-5-sulfonic acid and Na salt 2,2'-methylene bis-(6-(2H-benzotriazol-2-yl)-4-1,1,3,3-tetramethylbutyl) phenol) (Tinosorb®M)

phenylene bis-benzimidazyl tetrasulfonic acid disodium salt (Neo Heliopan®AP)

2,4-bis-[{(4-(2-ethylhexyloxy)-2-hydroxy}phenyl]-6-(4-methoxyphenyl)-1,3,5-triazine (Tinosorb® S)

benzylidene malonate polysiloxane (Parsol®SLX)

menthyl anthranilate (Neo Heliopan® MA)

2-(4-diethylamino-2-hydroxybenzoyl) benzoic acid hexyl ester (Uvinul® A Plus)

indanylidene compounds in accordance with DE 100 55 940(=WO 02/38537).

Advantageous primary and also secondary sun protection factors are mentioned in WO 2005 123101 A1. Advantageously, these preparations contain at least one UVA filter and/or at least one UVB filter and/or at least one inorganic pigment. The preparations may be present here in various forms such as are conventionally used for sun protection preparations. Thus, they may be in form of a solution, an emulsion of the water-in-oil type (W/O) or of the oil-in-water type (O/W) or a multiple emulsion, for example of the water-in-oil-in-water type (W/O/W), a gel, a hydrodispersion, a solid stick or else an aerosol.

In a further preferred embodiment a formulation according to the invention contains a total amount of sunscreen agents, i.e. in particular UV filters and/or inorganic pigments (UV filtering pigments) so that the formulation according to the invention has a light protection factor of greater than or equal to 2 (preferably greater than or equal to 5). Such formulations according to the invention are particularly suitable for protecting the skin and hair.

Secondary Sun Protection Factors

Besides the groups of primary sun protection factors mentioned above, secondary sun protection factors of the antioxidant type may also be used. Secondary sun protection factors of the antioxidant type interrupt the photochemical reaction chain which is initiated when UV rays penetrate into the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example alpha-carotene, beta-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, alpha-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages, also (metal) chelators (for example alpha-hydroxyfatty acids, palmitic acid, phytic acid, lactoferrine), alpha-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, superoxide dismutase, titanium dioxide (for example dispersions in ethanol), zinc and derivatives thereof (for example ZnO, ZnSO$_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

Advantageous inorganic secondary light protection pigments are finely dispersed metal oxides and metal salts which are also mentioned in WO 2005 123101 A1. The total quantity of inorganic pigments, in particular hydrophobic inorganic micro-pigments in the finished cosmetic preparation according to the present invention is advantageously from 0.1 to 30% by weight, preferably 0.5 to 10.0% by weight, in each case based on the total weight of the preparation.

Also preferred are particulate UV filters or inorganic pigments, which can optionally be hydrophobed, can be used, such as the oxides of titanium (TiO$_2$), zinc (ZnO), iron (Fe$_2$O$_3$), zirconium (ZrO$_2$), silicon (SiO$_2$), manganese (e.g. MnO), aluminium (Al$_2$O$_3$), cerium (e.g. Ce$_2$O$_3$) and/or mixtures thereof.

Actives Modulating Skin and/or Hair Pigmentation

Preferred active ingredients for skin and/or hair lightening are selected from the group consisting of: kojic acid (5-hydroxy-2-hydroxymethyl-4-pyranone), kojic acid derivatives, preferably kojic acid dipalmitate, arbutin, ascorbic acid, ascorbic acid derivatives, preferably magnesium ascorbyl phosphate, hydroquinone, hydroquinone derivatives, resorcinol, resorcinol derivatives, preferably 4-alkylresorcinols and 4-(1-phenylethyl)1,3-dihydroxybenzene (phenylethyl resorcinol), cyclohexylcarbamates (preferably one or more cyclohexyl carbamates disclosed in WO 2010/122178 and WO 2010/097480), sulfurcontaining molecules, preferably glutathione or cysteine, alpha-hydroxy acids (preferably citric acid, lactic acid, malic acid), salts and esters thereof, N-acetyl tyrosine and derivatives, undecenoyl phenylalanine, gluconic acid, chromone derivatives, preferably aloesin, flavonoids, 1-aminoethyl phosphinic acid, thiourea derivatives, ellagic acid, nicotinamide (niacinamide), zinc salts, preferably zinc chloride or zinc gluconate, thujaplicin and derivatives, triterpenes, preferably maslinic acid, sterols, preferably ergosterol, benzofuranones, preferably senkyunolide, vinyl guiacol, ethyl guiacol, dionic acids, preferably octodecene dionic acid and/or azelaic acid, inhibitors of nitrogen oxide synthesis, preferably L-nitroarginine and derivatives thereof, 2,7-dinitroindazole or thiocitrulline, metal chelators (preferably alpha-hydroxy fatty acids, phytic acid, humic acid, bile acid, bile extracts, EDTA, EGTA and derivatives thereof), retinoids, soy milk and extract, serine protease inhibitors or lipoic acid or other synthetic or natural active ingredients for skin and hair lightening, the latter preferably used in the form of an extract from plants, preferably bearberry extract, rice extract, papaya extract, turmeric extract, mulberry extract, bengkoang extract, nutgrass extract, liquorice root extract or constituents concentrated or isolated therefrom, preferably glabridin or licochalcone A, artocarpus extract, extract of *Rumex* and *Ramulus* species, extracts of pine species (*Pinus*), extracts of *Vitis* species or stilbene derivatives isolated or concentrated therefrom, saxifrage extract, scutelleria extract, grape extract and/or microalgae extract, in particular *Isochrysis galbana* Extract or *Tetraselmis suecica* Extract.

Preferred skin lighteners as component (b) are kojic acid and phenylethyl resorcinol as tyrosinase inhibitors, beta- and alpha-arbutin, hydroquinone, nicotinamide, dioic acid, Mg ascorbyl phosphate and vitamin C and its derivatives, mulberry extract, Bengkoang extract, papaya extract, turmeric extract, nutgrass extract, licorice extract (containing glycyrrhizin), alpha-hydroxy-acids, 4-alkylresorcinols, 4-hydroxyanisole. These skin lighteners are preferred due to their very good activity, in particular in combination with sclareolide according to the present invention. In addition, said preferred skin lighteners are readily available.

Advantageous skin and hair tanning active ingredients in this respect are substrates or substrate analogues of tyrosinase such as L-tyrosine, N-acetyl tyrosine, L-DOPA or L-dihydroxyphenylalanine, xanthine alkaloids such as caffeine, theobromine and theophyl-line and derivatives thereof, proopiomelanocortin peptides such as ACTH, alpha-MSH, peptide analogues thereof and other substances which bind to the melanocortin receptor, peptides such as Val-Gly-Val-Ala-Pro-Gly, Lys-Ile-Gly-Arg-Lys or Leu-Ile-Gly-Lys, purines, pyrimidines, folic acid, copper salts such as copper gluconate, chloride or pyrrolidonate, 1,3,4-oxadiazole-2-thiols such as 5-pyrazin-2-yl-1,3,4-oxadiazole-2-thiol, curcumin, zinc diglycinate (Zn(Gly)2), manganese(II) bicarbonate complexes ("pseudocat-alases") as described for example in EP 0 584 178, tetrasubstituted cyclohexene deriva-tives as described for example in WO 2005/032501, isoprenoids as described in WO 2005/102252 and in WO 2006/010661, melanin derivatives such as Melasyn-100 and MelanZe, diacyl glycerols, aliphatic or cyclic diols, psoralens, prostaglandins and ana-logues thereof, activators of adenylate cyclase and compounds which activate the transfer of melanosomes to keratinocytes such as serine proteases or agonists of the PAR-2 receptor, extracts of plants and plant parts of the *Chrysanthemum* species, *San-guisorba* species, walnut extracts, urucum extracts, rhubarb extracts, microalgae extracts, in particular *Isochrysis galbana*, trehalose, erythru-lose and dihydroxyacetone. Flavonoids which bring about skin and hair tinting or brown-ing (e.g. quercetin, rhamnetin, kaempferol, fisetin, genistein, daidzein, chrysin and api-genin, epicatechin, diosmin and diosmetin, morin, quercitrin, naringenin, hesperidin, phloridzin and phloretin) can also be used.

The amount of the aforementioned examples of additional active ingredients for the modulation of skin and hair pigmentation (one or more compounds) in the products according to the invention is then preferably 0.00001 to 30 wt. %, preferably 0.0001 to 20 wt. %, particularly preferably 0.001 to 5 wt. %, based on the total weight of the preparation.

Anti-Ageing Actives

In the context of the invention, anti-ageing or biogenic agents are, for example anti-oxidants, matrix-metalloproteinase inhibitors (MMPI), skin moisturizing agents, glycosaminglycan stimulkators, anti-inflammatory agents, TRPV1 antagonists and plant extracts.

Antioxidants. Suitable antioxidants encompass amino acids (preferably glycine, histidine, tyrosine, tryptophane) and derivatives thereof, imidazoles (preferably urocanic acid) and derivatives thereof, peptides, preferably D,L-carnosine, D-carnosine, L-carnosine and derivatives thereof (preferably anserine), carnitine, creatine, matrikine peptides (preferably lysyl-threonyl-threonyl-lysyl-serine) and palmitoylated pentapeptides, carotenoids, carotenes (preferably alpha-carotene, beta-carotene, lycopene) and derivatives thereof, lipoic acid and derivatives thereof (preferably dihydrolipoic acid), aurothioglucose, propyl thiouracil and other thiols (preferably thioredoxine, glutathione, cysteine, cystine, cystamine and glycosyl, N-acetyl, methyl, ethyl, propyl, amyl, butyl and lauryl, palmitoyl, oleyl, gamma-linoleyl, cholesteryl, glyceryl and oligoglyceryl esters thereof) and salts thereof, dilauryl thiodipropionate, distearyl thiodipropionate, thiodipropionic acid and derivatives thereof (preferably esters, ethers, peptides, lipids, nucleotides, nucleosides and salts) and sulfoximine compounds (preferably buthionine sulfoximines, homocysteine sulfoximine, buthionine sulfones, penta-, hexa-, heptathionine sulfoximine) in very small tolerated doses (e.g. pmol to μmol/kg), also (metal) chelators (preferably alpha-hydroxy fatty acids, palmitic acid, phytic acid, lactoferrin, alpha-hydroxy acids (preferably citric acid, lactic acid, malic acid), humic acid, bile acid, bile extracts, tannins, bilirubin, biliverdin, EDTA, EGTA and derivatives thereof), unsaturated fatty acids and derivatives thereof (preferably gamma-linolenic acid, linoleic acid, oleic acid), folic acid and derivatives thereof, ubiquinone and derivatives thereof, ubiquinol and derivatives thereof, vitamin C and derivatives (preferably ascorbyl palmitate, Mg ascorbyl phosphate, ascorbyl acetate, ascorbyl glucoside), tocopherols and derivatives (preferably vitamin E acetate), vitamin A and derivatives (vitamin A palmitate) and coniferyl benzoate of benzoic resin, rutinic acid and derivatives thereof, flavonoids and glycosylated precursors thereof, in particular quercetin and derivatives thereof, preferably alpha-glucosyl rutin, rosmarinic acid, carnosol, carnosolic acid, resveratrol, caffeic acid and derivatives thereof, sinapic acid and derivatives thereof, ferulic acid and derivatives thereof, curcuminoids, chlorogenic acid and derivatives thereof, retinoids, preferably retinyl palmitate, retinol or tretinoin, ursolic acid, levulinic acid, butyl hydroxytoluene, butyl hydroxyanisole, nordihydroguaiac acid, nordihydroguaiaretic acid, trihydroxybutyrophenone, uric acid and derivatives thereof, mannose and derivatives thereof, zinc and derivatives thereof (preferably ZnO, $ZnSO_4$), selenium and derivatives thereof (preferably selenium methionine), super-oxide dismutase, stilbenes and derivatives thereof (preferably stilbene oxide, trans-stilbene oxide) and the derivatives (salts, esters, ethers, sugars, nucleotides, nucleosides, peptides and lipids) of these cited active ingredients which are suitable according to the invention or extracts or fractions of plants having an antioxidant effect, preferably green tea, rooibos, honeybush, grape, rosemary, sage, melissa, thyme, lavender, olive, oats, cocoa, *Ginkgo, Ginseng*, liquorice, honeysuckle, sophora, *Pueraria, Pinus*, citrus, *Phyllanthus emblica* or St. John's wort, grape seeds, wheat germ, *Phyllanthus emblica*, coenzymes, preferably coenzyme Q10, plastoquinone and menaquinone. Preferred antioxidants are selected from the group consisting of vitamin A and derivatives, vitamin C and derivatives, tocopherol and derivatives, preferably tocopheryl acetate, and ubiquinone.

If vitamin E and/or derivatives thereof are used as the antioxidant(s), it is advantageous to choose their concentrations from the range from about 0.001 to about 10% b.w. based on the total weight of the formulation. If vitamin A or vitamin A derivatives or carotenes or derivatives thereof are used as the antioxidant(s), it is advantageous to choose their concentrations from the range from about 0.001 to about 10% b.w. based on the total weight of the formulation.

Matrix-Metalloproteinase inhibitors (MMPI). Preferred compositions comprise matrix-metalloproteinase inhibitors, especially those inhibiting matrix-metalloproteinases enzymatically cleaving collagen, selected from the group consisting of: ursolic acid, retinyl palmitate, propyl gallate, precocenes, 6-hydroxy-7-methoxy-2,2-dimethyl-1(2H)-benzopyran, 3,4-dihydro-6-hydroxy-7-methoxy-2,2-dimethyl-1(2H)-benzopyran, benzamidine hydrochloride, the cysteine proteinase inhibitors N-ethylmalemide and epsilon-amino-n-caproic acid of the serinprotease inhibitors: phenylmethylsufonylfluoride, collhibin (company Pentapharm; INCI: hydrolysed rice protein), oenotherol (company Soliance; INCI: propylene glycol, aqua, *Oenothera biennis* root extract, ellagic acid and ellagitannins, for example from pomegranate), phosphoramidone hinokitiol, EDTA, galardin, EquiStat (company Collaborative Group; apple fruit extract, soya seed extract, ursolic acid, soya isoflavones and soya proteins), sage extracts, MDI (company Atrium; INCI: glycosaminoglycans), fermiskin (company Silab/Mawi; INCI: water and lentinus edodes extract), actimp 1.9.3 (company Expanscience/Rahn; INCI: hydrolysed lupine protein), lipobelle soyaglycone (company Mibelle; INCI: alcohol, polysorbate 80, lecithin and soy isoflavones), extracts from green and black tea and further plant extracts, which are listed in WO 02 069992 A1 (see tables 1-12 there, incorporated herein by reference), proteins or glycoproteins from soya, hydrolysed proteins from rice, pea or lupine, plant extracts which inhibit MMPs, preferably extracts from shitake mushrooms, extracts from the leaves of the Rosaceae family, sub-family Rosoideae, quite particularly extracts of blackberry leaf (preferably as described in WO 2005 123101 A1, incorporated herein by reference) as e.g. SymMatrix (company Symrise, INCI: Maltodextrin, *Rubus Fruticosus* (Blackberry) Leaf Extract). Preferred actives of are selected from the group consisting of retinyl palmitate, ursolic acid, extracts from the leaves of the Rosaceae family, sub-family Rosoideae, genistein and daidzein.

Skin-moisturizing agents. Preferred skin moisturizing agents are selected from the group consisting of alkane diols or alkane triols comprising 3 to 12 carbon atoms, preferably $C_3$-$C_{10}$-alkane diols and $C_3$-$C_{10}$-alkane triols. More preferably the skin moisturizing agents are selected from the group consisting of: glycerol, 1,2-propylene glycol, 1,2-butylene glycol, 1,3-butylene glycol, 1,2-pentanediol, 1,2-hexanediol, 1,2-octanediol and 1,2-decanediol.

Glycosaminoglycan stimulators. Preferred compositions comprise substances stimulating the synthesis of glycosaminoglycans selected from the group consisting of hyaluronic acid and derivatives or salts, Subliskin (Sederma, INCI: Sinorhizobium Meliloti Ferment Filtrate, Cetyl Hydroxyethylcellulose, Lecithin), Hyalufix (BASF, INCI: Water, Butylene Glycol, *Alpinia galanga* leaf extract, Xanthan Gum, Caprylic/Capric Triglyceride), Stimulhyal (Soliance, INCI: Calcium ketogluconate), Syn-Glycan (DSM, INCI: Tetradecyl Aminobutyroylvalylaminobutyric Urea Trifluoroacetate, Glycerin, Magnesium chloride), Kalpariane (Biotech Marine), DC Upregulex (Distinctive Cosmetic Ingredients, INCI: Water, Butylene Glycol, Phospholipids, Hydrolyzed Sericin), glucosamine, N-acetyl glucosamine, retinoids, preferably retinol and vitamin A, Arctium lappa fruit extract, *Eriobotrya japonica* extract, Genkwanin, N-Methyl-L-serine, (−)-alpha-bisabolol or synthetic alpha-bisabolol such as e.g. Dragosantol and Dragosantol 100 from Symrise, oat glucan, *Echinacea purpurea* extract and soy protein hydrolysate. Preferred actives are selected from the group consisting of hyaluronic acid and derivatives or salts, retinol and derivatives, (−)-alpha-bisabolol or synthetic alpha-bisabolol such as e.g. Dragosantol and Dragosantol 100 from Symrise, oat glucan, *Echinacea purpurea* extract, Sinorhizobium Meliloti Ferment Filtrate, Calcium ketogluconate, *Alpinia galanga* leaf extract and tetradecyl aminobutyroylvalylaminobutyric urea trifluoroacetate.

TRPV1 antagonists. Suitable compounds which reduce the hypersensitivity of skin nerves based on their action as TRPV1 antagonists, encompass e.g. trans-4-tert-butyl cyclohexanol as described in WO 2009 087242 A1, or indirect modulators of TRPV1 by an activation of the µ-receptor, e.g. acetyl tetrapeptide-15, are preferred.

Desquamating agents. The compositions may also contain desquamating agents (component b5) in amounts of about 0.1 to about 30% b.w. preferably about 0.5 to about 15% b.w., particularly preferably about 1 to about 10% b.w. based on the total weight of the preparation. The expression "desquamating agent" is understood to mean any compound capable of acting:
- either directly on desquamation by promoting exfoliation, such as β-hydroxy acids, in particular salicylic acid and its derivatives (including 5-n-octanoylsalicylic acid); α-hydroxy acids, such as glycolic, citric, lactic, tartaric, malic or mandelic acids; urea; gentisic acid; oligofucoses; cinnamic acid; extract of *Sophora japonica*; resveratrol and some derivatives of jasmonic acid;
- or on the enzymes involved in the desquamation or the degradation of the corneodesmosomes, glycosidases, stratum corneum chymotryptic enzyme (SCCE) or other proteases (trypsin, chymotrypsin-like). There may be mentioned agents chelating inorganic salts: EDTA; N-acyl-N,N',N'-ethylenediaminetriacetic acid; aminosulphonic compounds and in particular (N-2-hydroxyethylpiperazine-N-2-ethane)sulphonic acid (HEPES); derivatives of 2-oxothiazolidine-4-carboxylic acid (procysteine); derivatives of alpha-amino acids of the glycine type (as described in EP-0 852 949, and sodium methylglycine diacetate marketed by BASF under the trade name TRILON M); honey; sugar derivatives such as O-octanoyl-6-D-maltose and N-acetylglucosamine; chestnut extracts such as those marketed by the company SILAB under the name Recoverine®, prickly pear extracts such as those marketed under the name Exfolactive® by the company SILAB, or Phytosphingosine SLC® (phytosphingosine grafted with a salicylic acid) marketed by the company Degussa.

Desquamating agents suitable for the invention may be chosen in particular from the group comprising sulphonic acids, calcium chelators, α-hydroxy acids such as glycolic, citric, lactic, tartaric, malic or mandelic acids; ascorbic acid and its derivatives such as ascorbyl glucoside and magnesium ascorbyl phosphate; nicotinamide; urea; (N-2-hydroxyethylpiperazine-N-2-ethane)sulphonic acid (HEPES), 3-hydroxy acids such as salicylic acid and its derivatives, retinoids such as retinol and its esters, retinal, retinoic acid and its derivatives, those described in the documents FR 2570377 A1, EP 0199636 A1, EP 0325540 A1, EP 0402072 A1, chestnut or prickly pear extracts, in particular marketed by SILAB; reducing compounds such as cysteine or cysteine precursors.

Desquamating agents which can be used are also nicotinic acid and its esters and nicotinamide, also called vitamin B3 or vitamin PP, and ascorbic acid and its precursors, as described in particular in application EP 1529522 A1.

Anti-cellulite agents. Anti-cellulite agents and lipolytic agents are preferably selected from the group consisting of those described in WO 2007/077541, and beta-adrenergic receptor agonists such as Synephrine and its derivatives, and cyclohexyl carbamates described in WO 2010/097479. Agents enhancing or boosting the activity of anti-cellulite agents, in particular agents which stimulate and/or depolarise C nerve fibres, are preferably selected from the group consisting of capsaicin and derivatives thereof, vanillylnonylamid and derivatives thereof, L-carnitine, coenzym A, isoflavonoides, soy extracts, ananas extract and conjugated linoleic acid.

Fat enhancing agents. Formulations and products according to the present invention may also comprise one or more fat enhancing and/or adipogenic agents as well as agents enhancing or boosting the activity of fat enhancing agents. A fat enhancing agent is for example hydroxymethoxyphenyl propylmethylmethoxybenzofuran (trade name: Sym3D®).

Hair Growth Activators or Inhibitors

Formulations and products according to the present invention may also comprise one or more hair growth activators, i.e. agents to stimulate hair growth. Hair growth activators are preferably selected from the group consisting of pyrimidine derivatives such as 2,4-diaminopyrimidine-3-oxide (Aminexil), 2,4-diamino-6-piperidinopyrimidine-3-oxide (Minoxidil) and derivatives thereof, 6-amino-1,2-dihydro-1-hydroxy-2-imino-4-piperidinopyrimidine and its derivatives, xanthine alkaloids such as caffeine, theobromine and theophylline and derivatives thereof, quercetin and derivatives, dihydroquercetin (taxifolin) and derivatives, potassium channel openers, antiandrogenic agents, synthetic or natural 5-reductase inhibitors, nicotinic acid esters such as tocopheryl nicotinate, benzyl nicotinate and C1-C6 alkyl nicotinate, proteins such as for example the tripeptide Lys-Pro-Val, diphencypren, hormons, finasteride, dutasteride, flutamide, bicalutamide, pregnane derivatives, progesterone and its derivatives, cyproterone acetate, spironolactone and other diuretics, calcineurin inhibitors such as FK506 (Tacrolimus, Fujimycin) and its derivatives, Cyclosporin A and derivatives thereof, zinc and zinc salts, polyphenols, procyanidins, proanthocyanidins, phytosterols such as for example beta-sitosterol, biotin, eugenol, (±)-beta-citronellol, panthenol, glycogen for example from mussels, extracts from microorganisms, algae, plants and plant parts of for example the genera dandelion (*Leontodon* or *Taraxa-*

*cum), Orthosiphon, Vitex, Coffea, Paullinia, Theobroma, Asiasarum, Cucurbita* or *Styphnolobium, Serenoa repens* (saw palmetto), *Sophora flavescens, Pygeum africanum, Panicum miliaceum, Cimicifuga racemosa, Glycine max, Eugenia caryophyllata, Cotinus coggygria, Hibiscus rosa-sinensis, Camellia sinensis, Ilex paraguariensis, lsochrysis galbana*, licorice, grape, apple, barley or hops or/nd hydrolysates from rice or wheat.

Alternatively, formulations and products according to the present invention may comprise one or more hair growth inhibitors (as described above), i.e. agents to reduce or prevent hair growth. Hair growth inhibitors are preferably selected from the group consisting of activin, activin derivatives or activin agonists, ornithine decarboxylase inhibitors such as alpha-difluoromethylornithine or pentacyclic triterpenes like for example ursolic acid, betulin, betulinic acid, oleanolic acid and derivatives thereof, 5alpha-reductase inhibitors, androgen receptor antagonists, S-adenosylmethionine decarboxylase inhibitors, gammaglutamyl transpeptidase inhibitors, transglutaminase inhibitors, soybean-derived serine protease inhibitors, extracts from microorganisms, algae, different microalgae or plants and plant parts of for example the families Leguminosae, Solanaceae, Graminae, Asclepiadaceae or Cucurbitaceae, the genera *Chondrus, Gloiopeltis, Ceramium, Durvillea, Glycine max, Sanguisorba officinalis, Calendula officinalis, Hamamelis virginiana, Arnica montana, Salix alba, Hypericum perforatum* or *Gymnema sylvestre*.

Physiological Cooling Agents

The compositions may also contain one or more substances with a physiological cooling effect (cooling agents), which are preferably selected here from the following list: menthol and menthol derivatives (for example L-menthol, D-menthol, racemic menthol, isomenthol, neoisomenthol, neomenthol) menthylethers (for example (I-menthoxy)-1,2-propandiol, (1-menthoxy)-2-methyl-1,2-propandiol, 1-menthyl-methylether), menthone glyceryl acetal, menthone glyceryl ketal or mixtures of both, menthylesters (for example menthylformiate, menthylacetate, menthylisobutyrate, menthyhydroxyisobutyrat, menthyllactates, L-menthyl-L-lactate, L-menthyl-D-lactate, menthyl-(2-methoxy)acetate, menthyl-(2-methoxyethoxy)acetate, menthylpyroglutamate), methylcarbonates (for example menthylpropyleneglycolcarbonate, menthylethyleneglycolcarbonate, menthylglycerolcarbonate or mixtures thereof), the semi-esters of menthols with a dicarboxylic acid or derivatives thereof (for example mono-menthylsuccinate, mono-menthylglutarate, monomenthylmalonate, O-menthyl succinic acid ester-N,N-(dimethyl)amide, O-menthyl succinic acid ester amide), menthanecarboxylic acid amides (in this case preferably menthanecarboxylic acid-N-ethylamide [WS3] or Na-(menthanecarbonyl)glycinethylester [WS5], as described in U.S. Pat. No. 4,150,052, menthanecarboxylic acid-N-(4-cyanophenyl)amide or menthanecarboxylic acid-N-(4-cyanomethylphenyl)amide as described in WO 2005 049553 A1, menthanecarboxylic acid-N-(alkoxyalkyl) amides), menthone and menthone derivatives (for example L-menthone glycerol ketal), 2,3-dimethyl-2-(2-propyl)-butyric acid derivatives (for example 2,3-dimethyl-2-(2-propyl)-butyric acid-N-methylamide [WS23]), isopulegol or its esters (I-(−)-isopulegol, I-(−)-isopulegolacetate), menthane derivatives (for example p-menthane-3,8-diol), cubebol or synthetic or natural mixtures, containing cubebol, pyrrolidone derivatives of cycloalkyldione derivatives (for example 3-methyl-2(1-pyrrolidinyl)-2-cyclopentene-1-one) or tetrahydropyrimidine-2-one (for example iciline or related compounds, as described in WO 2004/026840), further carboxamides (for example N-(2-(pyridin-2-yl) ethyl)-3-p-menthanecarboxamide or related compounds), (1R,2S,5R)—N-(4-Methoxyphenyl)-5-methyl-2-(1-isopropyl)cyclohexane-carboxamide [WS12], oxamates (preferably those described in EP 2033688 A2) and [(1R,2S,5R)-2-isopropyl-5-methylcyclohexyl] 2-(ethylamino)-2-oxo-acetate (X Cool).

Anti-Inflammatory Agents

The compositions may also contain anti-inflammatory and/or redness and/or itch ameliorating ingredients, in particular steroidal substances of the corticosteroid type selected from the group consisting of hydrocortisone, dexamethasone, dexamethasone phosphate, methyl prednisolone or cortisone, are advantageously used as anti-inflammatory active ingredients or active ingredients to relieve reddening and itching, the list of which can be extended by the addition of other steroidal anti-inflammatories. Non-steroidal anti-inflammatories can also be used. More particularly:

(i) steroidal anti-inflammatory substances of the corticosteroid type, in particular hydrocortisone, hydrocortisone derivatives such as hydrocortisone 17-butyrate, dexamethasone, dexamethasone phosphate, methyl-prednisolone or cortisone, (ii) non-steroidal anti-inflammatory substances, in particular oxicams such as piroxicam or tenoxicam, salicylates such as aspirin, disalcid, solprin or fendosal, acetic acid derivatives such as diclofenac, fenclofenac, indomethacin, sulindac, tolmetin or clindanac, fenamates such as mefenamic, meclofenamic, flufenamic or niflumic, propionic acid derivatives such as ibuprofen, naproxen or benoxaprofen, pyrazoles such as phenylbutazone, oxyphenylbutazone, febrazone or azapropazone, (iii) natural or naturally occuring anti-inflammatory substances or substances that alleviate reddening and/or itching, in particular extracts or fractions from camomile, Aloe vera, *Commiphora* species, *Rubia* species, willow, willow-herb, oats, calendula, arnica, St John's wort, honeysuckle, rosemary, *Passiflora incarnata*, witch hazel, ginger or *Echinacea*, or single active compounds thereof, (iv) histamine receptor antagonists, serine protease inhibitors (e.g. of Soy extracts), TRPV1 antagonists (e.g. 4-t-Butylcyclohexanol), NK1 antagonists (e.g. Aprepitant, Hydroxyphenyl Propamidobenzoic Acid), cannabinoid receptor agonists (e.g. Palmitoyl Ethanolamine) and TRPV3 antagonists.

Examples which can be cited here are oxicams such as piroxicam or tenoxicam; salicylates such as aspirin, disalcid, solprin or fendosal; acetic acid derivatives such as diclofenac, fenclofenac, indomethacin, sulindac, tolmetin or clindanac; fenamates such as mefenamic, meclofenamic, flufenamic or niflumic; propionic acid derivatives such as ibuprofen, naproxen, benoxaprofen or pyrazoles such as phenylbutazone, oxyphenylbutazone, febrazone or azapropazone. Anthranilic acid derivatives, in particular avenanthramides described in WO 2004 047833 A1, are preferred anti-itch ingredients in a composition according to the present invention.

Also useful are natural or naturally occurring anti-inflammatory mixtures of substances or mixtures of substances that alleviate reddening and/or itching, in particular extracts or fractions from camomile, Aloe vera, *Commiphora* species, *Rubia* species, willow, willow-herb, oats, calendula, arnica, St John's wort, honeysuckle, rosemary, *Passiflora incarnata*, witch hazel, ginger or *Echinacea*; preferably selected from the group consisting of extracts or fractions from camomile, *Aloe vera*, oats, calendula, arnica, honeysuckle, rosemary, witch hazel, ginger or *Echinacea*, and/or pure substances, preferably alpha-bisabolol, apigenin, apigenin-7-glucoside, gingerols, shogaols, gingerdiols, dehydrogingerdiones, paradols, natural or naturally occuring avenanthramides, preferably tranilast, avenanthramide A, avenanthramide B, avenanthramide C, non-natural or non-naturally occuring avenanthramides, preferably dihydroavenanthramide D, dihydroavenanthramide E, avenanthramide D, avenan-thramide E, avenanthramide F, boswellic acid, phytosterols, glycyrrhizin, glabridin and licochalcone A; preferably selected from the group consisting of alphabisabolol, natural avenanthramides, non-natural avenanthramides, preferably dihydroavenanthramide D (as described in WO 2004 047833 A1), boswellic acid, phytosterols, glycyrrhizin, and licochalcone A, and/or allantoin, panthenol, lanolin, (pseudo-)ceramides [preferably Ceramide 2, hydroxypropyl bispalmitamide MEA, cetyloxypropyl glyceryl methoxypropyl myristamide, N-(1-hexadecanoyl)-4-hydroxy-L-proline (1-hexadecyl) ester, hydroxyethyl palmityl oxyhydroxypropyl palmitamide], glycosphingolipids, phytosterols, chitosan, mannose, lactose and â-glucans, in particular 1,3-1,4-â-glucan from oats.

When bisabolol is used in the context of the present invention it can be of natural or synthetic origin, and is preferably "alpha-bisabolol". Preferably, the bisabolol used is synthetically prepared or natural (−)-alpha-bisabolol and/or synthetic mixed-isomer alpha-bisabolol. If natural (−)-alpha-bisabolol is used, this can also be employed as a constituent of an essential oil or of a plant extract or of a fraction thereof, for example as a constituent of (fractions of) oil or extracts of camomile or of *Vanillosmopsis* (in particular *Vanillosmopsis erythropappa* or *Vanillosmopsis arborea*). Synthetic alpha-bisabolol is obtainable, for example, under the name "Dragosantol" from Symrise.

In case ginger extract is used in the context of the present invention, preferably extracts of the fresh or dried ginger root are used which are prepared by extraction with methanol, ethanol, iso-propanol, acetone, ethyl acetate, carbon dioxide (CO2), hexane, methylene chloride, chloroform or other solvents or solvent mixtures of comparable polarity. The extracts are characterized by the presence of active skin irritation-reducing amounts of constituents such as e.g. gingerols, shogaols, gingerdiols, dehydrogingerdiones and/or paradols.

Anti-Microbial Agents

Suitable anti-microbial agents are, in principle, all substances effective against Gram-positive bacteria, such as, for example, 4-hydroxybenzoic acid and its salts and esters, N-(4-chlorophenyl)-N'-(3,4-dichlorophenyl)urea, 2,4,4'-trichloro-2'-hydroxy-diphenyl ether (triclosan), 4-chloro-3,5-dimethyl-phenol, 2,2'-methylenebis(6-bromo-4-chlorophenol), 3-methyl-4-(1-methylethyl)phenol, 2-benzyl-4-chloro-phenol, 3-(4-chlorophenoxy)-1,2-propanediol, 3-iodo-2-propynyl butylcarbamate, chlorhexidine, 3,4,4'-trichlorocarbanilide (TTC), antibacterial fragrances, thymol, thyme oil, eugenol, oil of cloves, menthol, mint oil, farnesol, phenoxyethanol, glycerol monocaprate, glycerol monocaprylate, glycerol monolaurate (GML), diglycerol monocaprate (DMC), salicylic acid N-alkylamides, such as, for example, n-octylsalicylamide or n-decylsalicylamide.

Enzyme Inhibitors

Suitable enzyme inhibitors are, for example, esterase inhibitors. These are preferably trialkyl citrates, such as trimethyl citrate, tripropyl citrate, triisopropyl citrate, tributyl citrate and, in particular, triethyl citrate (Hydagen CAT). The substances inhibit enzyme activity, thereby reducing the formation of odour. Other substances which are suitable esterase inhibitors are sterol sulfates or phosphates, such as, for example, lanosterol, cholesterol, campesterol, stigmasterol and sitosterol sulfate or phosphate, dicarboxylic acids and esters thereof, such as, for example, glutaric acid, monoethyl glutarate, diethyl glutarate, adipic acid, monoethyl adipate, diethyl adipate, malonic acid and diethyl malonate, hydroxycarboxylic acids and esters thereof, such as, for example, citric acid, malic acid, tartaric acid or diethyl tartrate, and zinc glycinate.

Odour Absorbers and Antiperspirant Active Agents

Suitable odour absorbers are substances which are able to absorb and largely retain odour-forming compounds. They lower the partial pressure of the individual components, thus also reducing their rate of diffusion. It is important that perfumes must remain unimpaired in this process. Odour absorbers are not effective against bacteria. They comprise, for example, as main constituent, a complex zinc salt of ricinoleic acid or specific, largely odour-neutral fragrances which are known to the person skilled in the art as "fixatives", such as, for example, extracts of labdanum or styrax or certain abietic acid derivatives. The odour masking agents are fragrances or perfume oils, which, in addition to their function as odour masking agents, give the deodorants their respective fragrance note. Perfume oils which may be mentioned are, for example, mixtures of natural and synthetic fragrances. Natural fragrances are extracts from flowers, stems and leaves, fruits, fruit peels, roots, woods, herbs and grasses, needles and branches, and resins and balsams. Also suitable are animal products, such as, for example, civet and castoreum. Typical synthetic fragrance compounds are products of the ester, ether, aldehyde, ketone, alcohol, and hydrocarbon type. Fragrance compounds of the ester type are, for example, benzyl acetate, p-tert-butylcyclohexyl acetate, linalyl acetate, phenylethyl acetate, linalyl benzoate, benzyl formate, allyl cyclohexylpropionate, styrallyl propionate and benzyl salicylate. The ethers include, for example, benzyl ethyl ether, and the aldehydes include, for example, the linear alkanals having 8 to 18 carbon atoms, citral, citronellal, citronellyloxyacetaldehyde, cyclamen aldehyde, hydroxycitronellal, lilial and bourgeonal, the ketones include, for example, the ionones and methyl cedryl ketone, the alcohols include anethole, citronellol, eugenol, isoeugenol, geraniol, linaool, phenylethyl alcohol and terpineol, and the hydrocarbons include mainly the terpenes and balsams. Preference is, however, given to using mixtures of different fragrances which together produce a pleasing fragrance note. Essential oils of relatively low volatility, which are mostly used as aroma components, are also suitable as perfume oils, e.g. sage oil, camomile oil, oil of cloves, melissa oil, mint oil, cinnamon leaf oil, linden flower oil, juniperberry oil, vetiver oil, olibanum oil, galbanum oil, labdanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, 3-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

Suitable astringent antiperspirant active ingredients are primarily salts of aluminium, zirconium or of zinc. Such suitable antihydrotic active ingredients are, for example, aluminium chloride, aluminium chlorohydrate, aluminium dichlorohydrate, aluminium sesquichlorohydrate and complex compounds thereof, e.g. with 1,2-propylene glycol, aluminium hydroxyallantoinate, aluminium chloride tartrate, aluminium zirconium trichlorohydrate, aluminium zirconium tetrachlorohydrate, aluminium zirconium pentachlorohydrate and complex compounds thereof, e.g. with amino acids, such as glycine.

Film Formers and Anti-Dandruff Agents

Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

Suitable antidandruff agents are Pirocton Olamin (1-hydroxy-4-methyl-6-(2,4,4-trimethylpentyl)-2-(1H)-pyridinone monoethanolamine salt), Baypival® (Climbazole), Ketoconazol® (4-acetyl-1-{4-[2-(2,4-dichlorophenyl) r-2-(1H-imidazol-1-ylmethyl)-1,3-dioxylan-c-4-ylmethoxyphenyl}-piperazine, ketoconazole, elubiol, selenium disulfide, colloidal sulfur, sulfur polyethylene glycol sorbitan monooleate, sulfur ricinol polyethoxylate, sulfur tar distillate, salicylic acid (or in combination with hexachlorophene), undecylenic acid, monoethanolamide sulfosuccinate Na salt, Lamepon® UD (protein/undecylenic acid condensate), zinc pyrithione, aluminium pyrithione and magnesium pyrithione/dipyrithione magnesium sulfate.

Preservatives

Suitable preservatives are, for example, phenoxyethanol, formaldehyde solution, parabens, 1,2-pentanediol or sorbic acid and the other classes of compounds listed in Appendix 6, Parts A and B of the Kosmetikverordnung ("Cosmetics Directive").

Perfume Oils and Fragrances

Suitable perfume oils are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamom, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, □-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable perfume. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Dyes

Suitable dyes are any of the substances suitable and approved for cosmetic purposes as listed, for example, in the publication "Kosmetische Färbemittel" of the Farbstoffkommission der Deutschen Forschungsgemeinschaft, Verlag Chemie, Weinheim, 1984, pages 81 to 106. Examples include cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). Luminol may also be present as a luminescent dye. Advantageous coloured pigments are for example titanium dioxide, mica, iron oxides (e.g. $Fe_2O_3$ $Fe_3O_4$, FeO (OH)) and/or tin oxide. Advantageous dyes are for example carmine, Berlin blue, chromium oxide green, ultramarine blue and/or manganese violet.

Preparations

Preferred compositions according to the present inventions are selected from the group of products for treatment, protecting, care and cleansing of the skin and/or hair or as a make-up product, preferably as a leave-on product (meaning that the one or more compounds of formula (I) stay on the skin and/or hair for a longer period of time, compared to rinse-off products, so that the moisturizing and/or anti-ageing and/or wound healing promoting action thereof is more pronounced).

The formulations according to the invention are preferably in the form of an emulsion, e.g. W/O (water-in-oil), O/W (oil-in-water), W/O/W (water-in-oil-in-water), O/W/O (oilin-water-in-oil) emulsion, PIT emulsion, Pickering emulsion, emulsion with a low oil content, micro- or nanoemulsion, a solution, e.g. in oil (fatty oils or fatty acid esters, in particular $C_6$-$C_{32}$ fatty acid $C_2$-$C_{30}$ esters) or silicone oil, dispersion, suspension, creme, lotion or milk, depending on the production method and ingredients, a gel (including hydrogel, hydrodispersion gel, oleogel), spray (e.g. pump spray or spray with propellant) or a foam or an impregnating solution for cosmetic wipes, a detergent, e.g. soap, synthetic detergent, liquid washing, shower and bath preparation, bath product (capsule, oil, tablet, salt, bath salt, soap, etc.), effervescent preparation, a skin care product such as e.g. an emulsion (as described above), ointment, paste, gel (as described above), oil, balsam, serum, powder (e.g. face powder, body powder), a mask, a pencil, stick, roll-on, pump, aerosol (foaming, non-foaming or post-foaming), a deodorant and/or antiperspirant, mouthwash and mouth rinse, a foot care product (including keratolytic, deodorant), an insect repellent, a sunscreen, aftersun preparation, a shaving product, aftershave balm, pre- and aftershave lotion, a depilatory agent, a hair care product such as e.g. shampoo (including 2-in-1 shampoo, anti-dandruff shampoo, baby shampoo, shampoo for dry scalps, concentrated shampoo), conditioner, hair tonic, hair water, hair rinse, styling creme, pomade, perm and setting lotion, hair spray, styling aid (e.g. gel or wax), hair smoothing agent (detangling agent, relaxer), hair dye such as e.g. temporary direct-dyeing hair dye, semi-permanent hair dye, permanent hair dye, hair conditioner, hair mousse, eye care product, make-up, make-up remover or baby product.

The formulations according to the invention are particularly preferably in the form of an emulsion, in particular in the form of a W/O, O/W, W/O/W, O/W/O emulsion, PIT emulsion, Pickering emulsion, emulsion with a low oil content, micro- or nanoemulsion, a gel (including hydrogel, hydrodispersion gel, oleogel), a solution e.g. in oil (fatty oils or fatty acid esters, in particular $C_6$-$C_{32}$ fatty acid $C_2$-$C_{30}$ esters)) or silicone oil, or a spray (e.g. pump spray or spray with propellant).

Auxiliary substances and additives can be included in quantities of 5 to 99% b.w., preferably 10 to 80% b.w., based on the total weight of the formulation. The amounts of cosmetic or dermatological auxiliary agents and additives and perfume to be used in each case can easily be determined by the person skilled in the art by simple trial and error, depending on the nature of the particular product.

The preparations can also contain water in a quantity of up to 99% b.w., preferably 5 to 80% b.w., based on the total weight of the preparation.

INDUSTRIAL APPLICATION

Another object of the present invention refers to the use of the mixtures as defined above for improving water resistance of skin care compositions and particularly sun care comprising primary and/or secondary sun protection filters.

Another object of the present invention refers to a method for simultaneously
- improving break resistance, volume, combability and lustre, and
- reducing split ends, fatigue and swelling of damaged, and particularly undamaged human hair by applying the mixture or the hair care composition, both defined above to human hair. For clarification the term "damaged hair" refers to human hair that contains an increased percentage of damage sites due to mechanical or chemical stress or environmental pollution, when compared to hair that has been subjected to regular combing only. Such kind of hair Is considered to be undamaged.

Further embodiments of the present invention refer to the use of the mixtures as defined above for
- improving break resistance, volume, combability and lustre of human hair, and/or
- reducing split ends, fatigue and swelling of human hair.

As explained above, these mixtures are preferably incorporated into a "two-in-one" shampoo, that is applied to hair when taking a shower.

Also these mixtures may be applied to damaged or undamaged human hair.

Although the best results in terms of combability are obtained applying a mixture of compounds (a) and (b) applicant has observed that also compound (a) when taken alone improves combability of dry and wet keratin fibres much better than other protein derivatives taken alone or in combination with conditioning agents.

Therefore, a final object of the present invention relates to the use of a protein extract obtained by a method comprising or consisting of the following steps (i) extracting dried cereal gluten under neutral conditions with an extraction medium comprising dilute alkanol so as to obtain a liquid extract comprising proteins, wherein the protein fraction of the extract consists essentially of prolamines;

(Ii) removing solid residue from the resulting liquid extract so as to produce a liquid phase;

(iii) treating said liquid phase with a polyhydric alcohol selected from the group consisting of glycerol and a short chain alkanediol; and (iv) concentrating the resultant treated liquid phase under reduced pressure until the resultant liquid concentrate has an alkanol content of less than 5 percent by weight for improving break resistance and combability of damaged, and particularly undamaged human hair.

Figure 2:
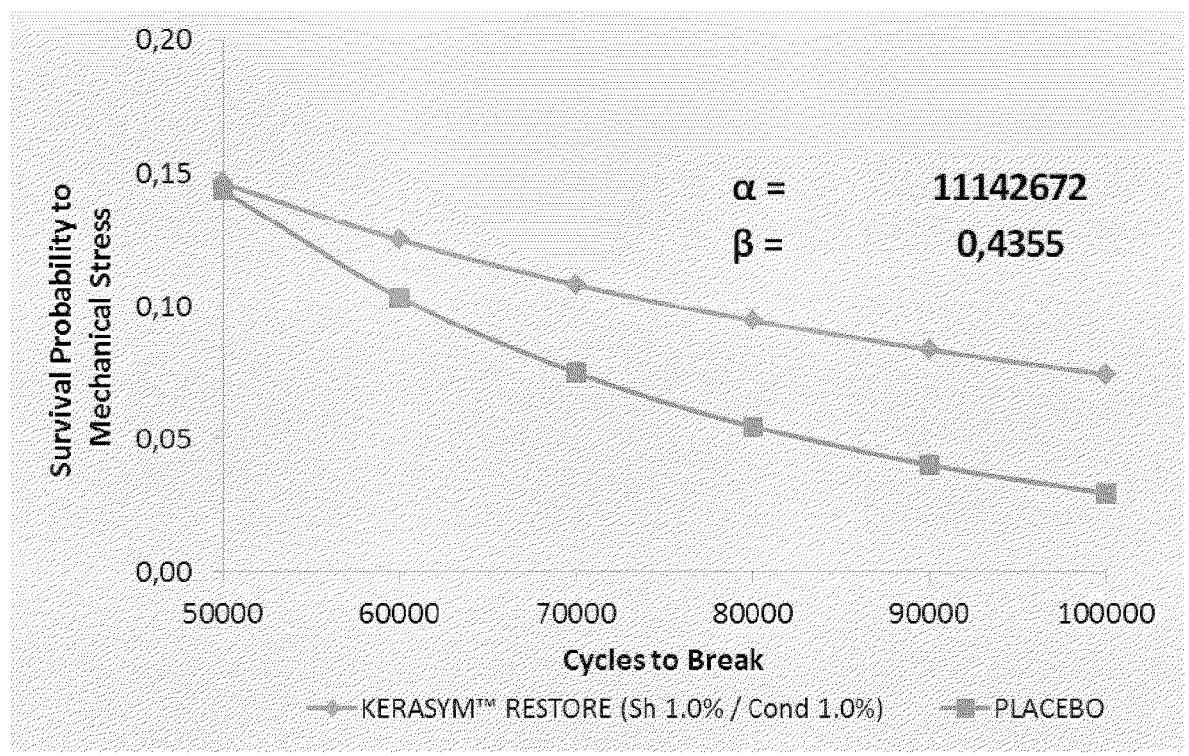
FIG. 2 is another graph illustrating performance of the present invention.

The invention is illustrated—but not limited—by the following examples. FIGS. 1 and 2 in the annex show survival probability due to mechanical stress for formulation D (Fatigue test).

EXAMPLES

Preparation of the Protein Extract

Commercially available, dried wheat gluten is extracted with 50-90 percent, preferably 60-70 percent, ethanol in a ratio of wheat gluten to solvent of from 1:15 to 1:2, preferably from 1:10 to 1:5, at 15-45 degrees centigrade, preferably at 20 to 30 degrees centigrade.

After the mixture has been stirred for 0.25-48 h, preferably 1 to 4 h, the suspension is freed from most of the solid phase using a decanter. The resulting decanted liquid is filtered until clear by filtration using a plate filter. The glycerol is then added and the mixture is evaporated under reduced pressure. Water and ethanol are distilled off until the bottom product contains less than about 1 percent ethanol. The resulting product can contain 1-30 percent by weight of protein and normally contains about 10 percent by weight of protein (dry substance).

In place of, or together with, ethanol, it is also possible to use methanol and/or isopropanol in appropriate dilution for the extraction, and the glycerol can be replaced in whole or in part by an alkanediol, such as ethylene glycol or propylene glycol. The product is sold by the applicant under the trademark SymHair® Restore.

Example 1

Formulation Properties

A protein extract solution in glycerin prepared as described above containing 9 to 11 percent by weight of protein (dry substance) was divided into two portions. One portion was used as such and to the other portion 1% of a 10% aqueous citric acid solution(=0.1% citric acid absolute) was added. Each sample was dissolved at 3% in water and the appearance was evaluated visually. The results are shown in Table 1:

TABLE 1

Results of visual evaluation

|  | Protein extract solution without citric acid | Protein extract solution with 0.1% citric acid* |
|---|---|---|
| Appearance | Highly turbid solution | Slightly turbid solution |

*addition of 1% of a 10% aqueous citric acid solution

Then, the protein solution with or without 0.1% citric acid was dosed at 3% into a clear shampoo formulation and again the appearance was evaluated visually. Following Tables 2 and 3 show a shampoo formulation and the results of visual evaluation

TABLE 2

Shampoo formula (amounts in wt.-%)

| Raw Material | INCI | Amount |
|---|---|---|
| Plantacare ® PS10 | Sodium Laureth Sulfate, Lauryl Glycoside | 17.0 |
| Citric Acid | Citric Acid | 0.15 |
| SymDiol ® 68 | 1,2 Hexandiol, Caprylyl Glycol | 1.0 |
| EDTA BD | Disodium EDTA | 0.1 |
| Sodium Chloride | Sodium Chloride | 0.4 |
| Water, demineralized | Water (Aqua) | Ad 100 |
| Ucare Polymer JR-400 | Polyquaternium-10 | 0.2 |
| Potassium Sorbate | Potassium Sorbate | 0.15 |
| Tego ® Betaine F50 | Cocoamidoproyl Betaine | 5.0 |

TABLE 3

Results of visual evaluation

|  | Shampoo with protein extract solution without citric acid | Shampoo with protein extract solution with 0.1% citric acid |
|---|---|---|
| Appearance | Highly turbid | Clear |

Addition of citric acid to the protein extract solution gives a clear improvement of formulation properties. The clear shampoo stays clear. The protein solution with or without 0.1% citric acid was also dosed at 3% into a clear gel formulation and again the appearance was evaluated visually. Tables 4 and 5 show a gel formula and its visual evaluation.

TABLE 4

Gel formula (all amounts in wt.-%)

| Raw Material | INCI | Amount |
|---|---|---|
| EDTA BD | Disodium EDTA | 0.1 |
| Glycerine | Glycerine | 3.0 |
| SymOcide ® PH | Phenoxyethanol, Hydroxyacetophenone, Caprylyl Glycol, Aqua | 0.5 |
| Keltrol ® CG-T | Xanthan Gum | 0.1 |
| Aristoflex ® AVC | Ammonium Acryloyoldimethyltaurate/VP Copolymer | 2.0 |
| Propylene Glycol | Propylene Glycol | 1.5 |
| Sodium Hydroxide 10% solution | Aqua, Sodium Hydroxide | 0.15 |
| Hydrolite ® 5 | Pentylene Glycol | 4.0 |
| Ethanol 96% | Alcohol Denaturized | 18.0 |
| Water, demineralized | Water (Aqua) | Ad 100 |

TABLE 5

Results of visual evaluation

|  | Gel with protein extract solution without citric acid | Gel with protein extract solution with 0.1% citric acid |
|---|---|---|
| Appearance | Highly turbid | Clear |

Addition of citric acid to the protein extract solution gives a clear improvement of formulation properties. The clear gel stays clear.

Example 2

Characterization of Protein Size Distribution by Gel Electrophoresis

Figure 3:
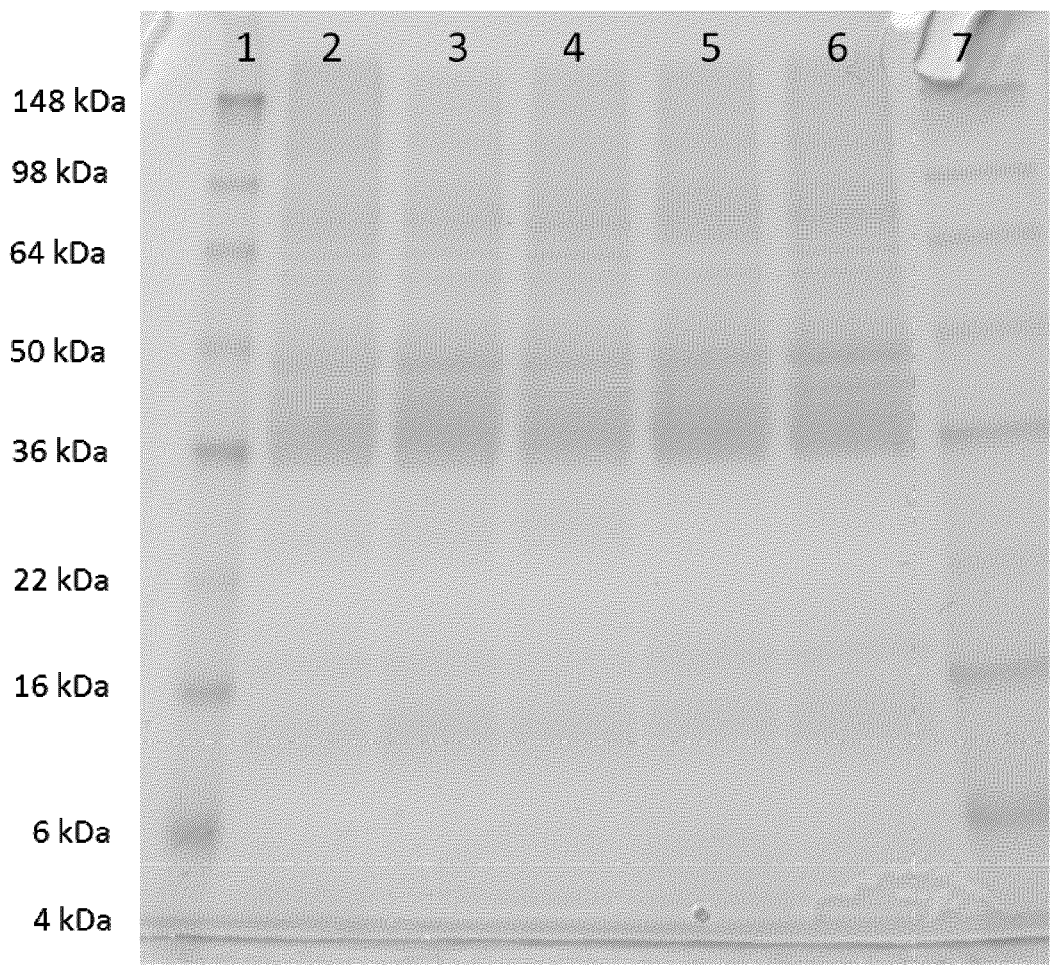
FIG. 3 illustrates performance of the present invention.

Five protein extract solutions in glycerin containing 9 to 11 percent by weight of protein (dry substance) were prepared from different batches of wheat gluten and the solutions were acidified by addition of citric acid as described above. The protein size distribution was analyzed by sodium dodecyl sulfate polyacrylamide gel electrophoresis (SDS-PAGE). After the dilution of the protein extract solutions in water, SDS-puffer and loading-puffer were added. The samples were denatured at 65° C. for 5 minutes. Subsequently, the samples were loaded up on the gel (10-20% Criterion™ TGX™ Precast Midi Protein Gel). The SDS-PAGE was running for 25 minutes at a constant voltage of 300 V. To visualize the proteins after the electrophoresis, the gel was stained with Quick Coomassie® Stain. The results are shown in FIG. 3 (SDS-Page stained with Quick Coomassie® Stain)

Lane 1 and 7 SeeBlue™ Plus2 Pre-Stained Protein Standard

Lane 2 to 6 Protein extract solutions, 1% diluted in water in triplicate

According to SDS-PAGE, the majority of the contained proteins have a molecular weight >22 kDa. Semi-quantitative determination of the protein composition was performed by densitometry analysis of the SDS-Page by using the software ImageJ To calculate e.g. the percentage ratio of proteins under 22 kDa, the amount of pixels under the marker bond of 22 kDa is compared to the total amount of pixels. Results are given as mean values of the 5 samples. The results are shown in Table 6.

TABLE 6

Results of densitometry analysis

| Parameter | Mean values |
|---|---|
| Sum all pixel | 304.530.080 ± 20.447.480 |
| Sum pixel <22 kDa | 103.921.283 ± 10.160.848 |
| Sum pixel >22 kDa | 200.608.797 ± 10.286.633 |
| Sum pixel 22-50 kDa | 97.611.360 ± 3.979.818 |
| Sum pixel >50 kDa | 102.997.437 ± 6.395.194 |
| Ratio <22 kDa [%] | 34.03 ± 1.05 |
| Ratio >22 kDa [%] | 65.97 ± 1.05 |
| Ratio 22-50 kDa [%] | 32.13 ± 1.30 |
| Ratio >50 kDa [%] | 33.84 ± 1.32 |

The results show that in mean 34% of the proteins are smaller than 22 kDa and 66% are bigger than 22 kDa. The 66% of proteins being bigger than 22 kDa are a sum of 32% being in the range of 22 to 50 kDa and 34% being bigger than 50 kDa.

Standard Formulations

The following examples were performed with standard a shampoo or a "2-in-1" shampoo and conditioner formulation.

Formulation C0 stands for a control, comprising neither a protein derivative nor a conditioning agent. Formulations C1 and C2 serve for comparison, the first one comprising a hydrolyzed wheat protein, but no conditioning agent, the other comprising a mixture with Cationized starch as the conditioning agent. Both compounds were added in amounts of 1% b.w.

Formulations A and B are working examples according to the invention, comprising SymHair® Restore which is a protein extract based on wheat gluten as explained in the specification; the compound is added in amounts of 0.5 and 1% b.w. Formulations C and D are also according to the invention and comprise mixtures of said wheat extract and cationized starch as the conditioning agent in a ration by weight of 1:1. The components are added each in amounts of 0.5 and 1% by weight respectively.

Example 3

Dry and Wet Combability

Combability of dry and wet strains of Caucasian hair was determined by measuring the combing energy after applying the test formulations to dry and wet hair strains. The results are presented in Table 7.

TABLE 7

| Combability of dry and wet hair strains | | | | | | | |
|---|---|---|---|---|---|---|---|
| Ingredients | C0 | C1 | C2 | A | B | C | D |
| Sodium Laureth Sulfate | 10.0 | 10.0 | 10.0 | 10.0 | 10.0 | 10.0 | 10.0 |
| Cocamidopropyl Betaine | 8.0 | 8.0 | 8.0 | 8.0 | 8.0 | 8.0 | 8.0 |
| Coco Glucosides | 4.0 | 4.0 | 4.0 | 4.0 | 4.0 | 4.0 | 4.0 |
| SymHair ® Restore | — | — | — | 0.5 | 1.0 | 0.5 | 1.0 |
| Hydrolyzes wheat proteins | — | 1.0 | 1.0 | — | — | — | — |
| Cationized starch | — | — | 1.0 | — | — | 0.5 | 1.0 |
| Water | | | | Ad 100 | | | |
| Combability (dry) | | | | | | | |
| Combing energy (J) | 0.055 | 0.035 | 0.033 | 0.029 | 0.027 | 0.025 | 0.024 |
| Reduction vs. control (%) | — | 36 | 40 | 48 | 50 | 55 | 57 |
| Combability (wet) | | | | | | | |
| Combing energy (J) | 0.050 | 0.035 | 0.033 | 0.033 | 0.031 | 0.030 | 0.029 |
| Reduction vs. control (%) | — | 31 | 35 | 35 | 38 | 40 | 43 |

Compared to the comparative formulations the protein extract forming compound (a) leads to a significant reduction in combing energy, both in terms of dry and wet hair. For dry hair the effect is for SymHair® Restore (10% gluten extract, 0.05% citric acid, and 0.5 wt.-% ethanol, glycerol at 100 wt.-%) at 0.5% higher than for the mixture using the hydrolysate and the conditioning agent at 1% each, for wet hair the effect at 0.5% alone is the same as for the comparative formulation at 1% each. The superiority in combing performance can be further improved by blending SymHair® Restore with a conditioning agent.

Example 4

Split Ends Repair

The repair effect of the test formulations was measured by monitoring the amount of split ends under the microscope before and after the treatment. The results are presented in Table 8.

TABLE 8

| Split Ends Repair | | | | | | | |
|---|---|---|---|---|---|---|---|
| Ingredients | C0 | C1 | C2 | A | B | C | D |
| Sodium Laureth Sulfate | 10.0 | 10.0 | 10.0 | 10.0 | 10.0 | 10.0 | 10.0 |
| Cocamidopropyl Betaine | 8.0 | 8.0 | 8.0 | 8.0 | 8.0 | 8.0 | 8.0 |
| Coco Glucosides | 4.0 | 4.0 | 4.0 | 4.0 | 4.0 | 4.0 | 4.0 |
| SymHair ® Restore | — | — | — | 0.5 | 1.0 | 0.5 | 1.0 |
| Esterquats[1] | — | 1.0 | 1.0 | — | — | — | — |
| Cationized starch | — | — | 1.0 | — | — | 0.5 | 1.0 |
| Water | | | | Ad 100 | | | |
| Split Ends Reduction (%) | | | | | | | |
| Numbers | 43 | 40 | 39 | 38 | 37 | 37 | 35 |
| Reduction vs. control (%) | — | 8 | 10 | 12 | 15 | 14 | 17 |

[1]Dehyquart ® AU46 (BASF Nutrition & Personal Care GmbH)

Examples and comparative examples clearly indicate that the mixtures according to the present invention improve split repair and reduce numbers of split ends.

Example 5

Break Resistance and Swelling

Break resistance was measured by determining the number of fragments after applying the test formulations versus the control and the microscope. Swelling of the fibers was also detected under microscope. The results are presented in Table 9.

TABLE 9

Break resistance and swelling

| Ingredients | C0 | C1 | C2 | A | B | C | D |
|---|---|---|---|---|---|---|---|
| Sodium Laureth Sulfate | 10.0 | 10.0 | 10.0 | 10.0 | 10.0 | 10.0 | 10.0 |
| Cocamidopropyl Betaine | 8.0 | 8.0 | 8.0 | 8.0 | 8.0 | 8.0 | 8.0 |
| Coco Glucosides | 4.0 | 4.0 | 4.0 | 4.0 | 4.0 | 4.0 | 4.0 |
| SymHair ® Restore | — | — | — | 0.5 | 1.0 | 0.5 | 1.0 |
| Hydrolyzes wheat proteins | — | 1.0 | 1.0 | — | — | — | — |
| Dimethicone | — | — | 1.0 | — | — | 0.5 | 1.0 |
| Water | | | | Ad 100 | | | |
| Break resistance | | | | | | | |
| Number of fragments | 51 | 43 | 41 | 39 | 38 | 38 | 36 |
| Reduction vs. control (%) | — | 15 | 19 | 24 | 25 | 26 | 28 |
| Swelling (%) | | | | | | | |
| Swelling of fibers | 30 | 20 | 19 | 15 | 14 | 13 | 13 |
| Reduction vs. control (%) | — | 35 | 38 | 50 | 53 | 55 | 57 |

Examples and comparative examples clearly indicate that the mixtures according to the present invention improve break resistance and reduce swelling of the keratin fibers.

Example 6

Tensile Strength

Tensile strength of Caucasian bleached hair and Straightened Afro hair was determined by measuring stress and elastic module before after treatment with the test formulations versus control. The results are presented in Table 10.

TABLE 10

Tensile strength

| Ingredients | C0 | C1 | C2 | A | B | C | D |
|---|---|---|---|---|---|---|---|
| Sodium Laureth Sulfate | 10.0 | 10.0 | 10.0 | 10.0 | 10.0 | 10.0 | 10.0 |
| Cocamidopropyl Betaine | 8.0 | 8.0 | 8.0 | 8.0 | 8.0 | 8.0 | 8.0 |
| Coco Glucosides | 4.0 | 4.0 | 4.0 | 4.0 | 4.0 | 4.0 | 4.0 |
| SymHair ® Restore | — | — | — | 0.5 | 1.0 | 0.5 | 1.0 |
| Hydrolyzes wheat proteins | — | 1.0 | 1.0 | — | — | — | — |
| Cationic Hydroxyethylcellulose[2] | — | — | 1.0 | — | — | 0.5 | 1.0 |
| Water | | | | Ad 100 | | | |
| Caucasian bleached hair | | | | | | | |
| Stress (gmf/µm$^2$) | 0.0101 | 0.0106 | 0.0108 | — | — | 0.0112 | 0.0124 |
| Improvement vs*. Control (%) | — | 5 | 7 | — | — | 10 | 23 |
| Elastic module (N/m$^2$) | 3.0E9 | 3.0E9 | 3.0E9 | — | — | 3.2E9 | 3.2E9 |
| Improvement vs. control (%) | — | 2 | 4 | — | — | 9 | 15 |
| Straightened Afro hair | | | | | | | |
| Stress (gmf/µm$^2$) | 0.0112 | 0.0115 | 0.0116 | — | — | 0.0121 | 0.0121 |
| Improvement vs. control (%) | — | 3 | 3 | — | — | 8 | 8 |
| Elastic module (N/m$^2$) | 3.8E9 | 3.8E9 | 3.8E9 | — | — | 4.0E9 | 4.0E9 |
| Improvement vs. control (%) | — | | | — | — | 10 | 10 |

[2]Polymer JR 400 (Amerchol)

Examples and comparative examples clearly indicate that the mixtures according to the present invention improve tensile strength and elastic module of the keratin fibers.

Example 7

Water Resistance

Effect of addition of SymHair Restore on in vitro water resistance properties of a skin care sunscreen formulation was evaluated. Natural sheep wool, 390-430 g/m$^2$ (KWL Texil GmbH) was machine-washed twice at 30° C., without pre-washing cycle with unperfumed light-duty detergent. Afterwards it was dried at room temperature (RT). 0.100-0.150 g of the test product (formula given in table 11) was applied evenly on 4 pieces of sheep wool fabric (5×10 cm) and the amount was exactly weighed back. After drying for at least 30 minutes at RT, 2 of the pieces were attached to a stirrer and immersed in a beaker filled with 4.5 l of stirred tap water at 20-25° C. for 80 minutes (stirrer with wool piece: 100 rpm, magnetic stirrer: 200 rpm). Then the fabric was dried for at least 12 hours at RT. The remaining 2 untreated pieces of wool which were not immersed in water were used as reference.

To determine the in vitro water resistance, the watered and un-watered fabric samples were boiled with 60-80 g of isopropyl alcohol each for 10 minutes and then cooled down to ambient temperature. The resulting solution was filled in a 100 ml graduated flask and the volume was adjusted to the level mark. After filtration, the absorbance (290-400 nm, cuvette: 1,00 mm) of the solution was measured with a UV/Vis Spectrometer and the absorbance maximum was determined.

Substantivity, i.e. in vitro water resistance, was calculated according to the following equation:

$$\text{Substantivity } S\ (\%) = \frac{UV_{max}(\text{after water immersion}) \times m(\text{without water immersion})}{UV_{max}(\text{without water immersion}) \times m(\text{after water immersion})} \times 100$$

The results are presented in Table 11.

TABLE 11

In vitro water resistance

| Phase | Ingredients | INCI-Name | C1 | B |
|---|---|---|---|---|
| A | Emulsiphos | Potassium Cetyl Phosphate, Hydrogenated Palm Glycerides | 1.50 | 1.50 |
|  | Finsolv TN | C12-15 Alkyl Benzoate | 3.00 | 3.00 |
|  | Copherol 1250 | Tocopheryl Acetate | 0.50 | 0.50 |
|  | Lanette O | Cetearyl Alcohol | 1.00 | 1.00 |
|  | Dow Corning 246 Fluid | Cyclohexasiloxane | 2.00 | 2.00 |
|  | Neo Heliopan ® 357 | Butyl Methoxydibenzoylmethane | 1.50 | 1.50 |
|  | Neo Heliopan ® OS | Ethylhexyl Salicylate | 5.00 | 5.00 |
|  | Neo Heliopan ® AV | Ethylhexyl Methoxycinnamate | 3.00 | 3.00 |
|  | EDTA BD | Disodium EDTA | 0.10 | 0.10 |
|  | Keltrol T | Xanthan Gum | 0.20 | 0.20 |
|  | Carbopol EDT 2050 | Carbomer | 0.20 | 0.20 |
| B | Demineralized Water | Water (Aqua) | Ad 100 | Ad 100 |
|  | Glycerin 99% | Glycerin | 4.70 | 4.70 |
|  | Dragocid Liquid | Phenoxyethanol, Methylparaben, Ethylparaben, Butylparaben, Propylparaben, Isobutylparaben | 0.70 | 0.70 |
|  | Neo Heliopan ® Hydro | Phenylbenzimidazole Sulfonic Acid used as a 30% solution neutralized with TEA | 6.67 | 6.67 |
|  | Hydrolite -5 | Pentylene Glycol | — | — |
| C | Triethanolamin | Triethanolamine | 0.60 | 0.60 |
| D | SymHair Restore | Glycerin, Triticum Vulgare (Wheat) Protein, Water | — | 2.00 |
|  | Perfume | Fragrance (Parfum) | 0.40 | 0.40 |
|  | Dragosantol 100 | Bisabolol | 0.10 | 0.10 |
|  | Colour after manufacturing |  | white | white |
|  | pH value |  | 7.4 | 7.4 |
|  | in vitro water resistance (at 309 nm) S in percent |  | 74.0 | 81.0% |

The results clearly show an improvement of in vitro water resistance (substantivity) by addition of 2% of SymHair Restore to the sun protection skin care formula.

Hair Care Formulations

Example A

Gentle Co Wash, Strong Restoration (All Amounts in wt.-%)

| Phase | Component | INCI | Amount |
|---|---|---|---|
| A | Water | Water (Aqua) | 80.10 |
|  | Jaguar EXCEL | Guar Hydroxypropyltrimonium Chloride | 0.30 |
|  | SymOcide ®PH | Phenoxyethanol, Hydroxyacetophenone, Caprylyl Glycol, Water (Aqua) | 1.40 |
| B | Lanette ® 16 | Cetyl alcohol | 3.50 |
|  | Lanette ®18 | Stearyl alcohol | 2.50 |
|  | Incroquat ® Behenyl TMS | Cetearyl Alcohol and Behentrimonium Methosulfate | 3.00 |
|  | Brazilian Nut Oil | Brazilian Nut Oil | 2.00 |
|  | SymMollient ® S | Cetearyl Nonanoate | 1.00 |
| C | SymHair ® Restore | Glycerin, Triticum Vulgare (Wheat) Protein, Water | 1.00 |

-continued

| Phase | Component | INCI | Amount |
|---|---|---|---|
| | SymHair ® Shape | *Triticum Vulgare* Bran Extract Linoleic acid, Cetearyl Nonanoate, ethylhexyl isononanoate, *Camellia Oleifera* Seed Oil, Tocopherol | 0.50 |
| | PMX-200 Silicone Fluid 350 CS | Dimethicone | 1.00 |
| | Perfume (788691) | Fragrance | 1.20 |
| | Plantacare ® 1200 UP | Lauryl glucoside | 2.50 |

Example B

Restoring Shampoo (All Amounts in wt.-%)

| Phase | Component | INCI | Amount |
|---|---|---|---|
| A | Water | Water (Aqua) | ad 100.00 |
| | Disodium EDTA | Disodium EDTA | 0.05 |
| | Glycerine | Glycerine | 1.00 |
| | Sensomer 10M polymer | Polyquaternium-10 | 0.20 |
| B | Alkopon N | Sodium Laureth Sulfate | 29.63 |
| | Alkolan CP 30 EG | Cocamidopropyl Betaine | 2.00 |
| | SymDiol ® 68 | 1.2-Hexanediol. Caprylyl Glycol | 0.80 |
| | SymMollient ® W/S | Trideceth-9. PEG-5 Isononanoate. Water | 1.00 |
| C | Myrj ® 6000 | PEG-150 Distearate | 0.50 |
| | Alkolan PK 2H | Cocamide DEA | 1.50 |
| D | Sodium Chloride | Sodium Chloride | 0.15 |
| | Perfume (948871) | Fragrance | 0.5 |
| | SymHair ® Restore | Glycerin. *Triticum Vulgare* (Wheat) Protein. Water | 1.00 |

Example C

Hair Care Speed Ampoule Composition (All Amounts in wt.-%)

| Phase | Component | INCI | Amount |
|---|---|---|---|
| A | Lanette O | Cetearyl alcohol | 4.00 |
| | Emulsiphos ® | Potassium Cetyl Phosphate. Hydrogenated Palm Glycerides | 1.00 |
| | Isodragol ® | Triisononanoin | 3.00 |
| | Incroquat ® Behenyl TMS | Cetearyl Alcohol and Behentrimonium Methosulfate | 4.50 |
| | Brazilian Nut Oil | *Bertholletia Excelsa* Seed Oil | 3.00 |
| | Passion Fruit Oil | *Passiflora Edulis* Seed Oil | 3.00 |
| | Lanette ® 18 | Stearyl alcohol | 1.00 |
| B | Cupuacu butter | *Theobroma Grandiflorum* Seed Butter | 2.00 |
| | Water | Water (Aqua) | ad 100 |
| | Jaguar EXCEL | Guar Hydroxypropyltrimonium Chloride | 0.30 |
| | Natrosol 250 HHR | Hydroxyethylcellulose | 0.30 |
| | EDTA Disodium (800130) | Disodium EDTA | 0.10 |
| C | Frescolat ® ML | Menthyl Lactate | 0.50 |
| | Hydrolite ® 5 | Pentylene Glycol | 3.00 |
| | SymOcide ® PH | Phenoxyethanol. Hydroxyacetophenone. Caprylyl Glycol. Water (Aqua) | 1.40 |
| D | Aqua | Aqua | 10.00 |
| | Ucare polymer JR-400 | Polyquaternium-10 | 0.20 |
| E | SymHair ® Shape | *Triticum Vulgare* Bran Extract Linoleic acid. Cetearyl Nonanoate. ethylhexyl isononanoate. *Camellia Oleifera* Seed Oil. Tocopherol | 0.50 |
| | SymHair ® Restore | Glycerin. *Triticum Vulgare* (Wheat) Protein. Water | 1.00 |
| | Perfume (788690) | Fragrance | 1.00 |
| | Citric Acid 30% | Citric Acid. Water | qs |

Example D

Anti-Damage Composition for Hair Care (All Amounts in wt.-%)

| Phase | Component | INCI | Amount |
|---|---|---|---|
| A | Water | (Water) Aqua | Ad 100 |
|   | Glycerine | Glycerine | 1.00 |
|   | Symsave ® H | Hydroxyacetophenone | 0.50 |
|   | Symdiol ® 68 | 1.2-Hexanediol. Caprylyl Glycol | 0.50 |
| B | Tego Amide S18 | Dimethylaminopropyl Stearamide | 2.50 |
| C | Varisoft EQ 65 | Distearoylethyl Dimonium Chloride; Cetearyl Alcohol | 3.00 |
|   | SymMollient ® S | Cetearyl Nonanoate | 2.00 |
|   | Shea Butter (refined) | *Butyrospermum Parkii* (Shea) Butter | 3.00 |
|   | Mineral Oil | Mineral Oil | 1.50 |
|   | Andiroba Oil | *Carapa Guaianensis* Seed Oil | 1.00 |
|   | Keto-Stearyl Alcohol 30/70 | Cetearyl Alcohol | 4.50 |
|   | Alkonat 1698 | Cetyl Alcohol | 3.00 |
|   | Isopropyl Myristate | Isopropyl Miristate | 2.00 |
| D | Perfume (702525) | Fragrance | 0.50 |
|   | SymHair ® Restore | Glycerin. *Triticum Vulgare* (Wheat) Protein. Water | 1.00 |
| E | Hydromoist ® O | Water (Aqua). *Avena Sativa* (Oat) Peptide | 0.50 |
|   | Actipone ® Black Rice GW | Water (Aqua). Glycerin. *Oryza Sativa* (Rice) Extract | 0.50 |
|   | Extrapone ® Rice GW | Glycerin. Water (Aqua). PEG-40 Hydrogenated Castor Oil. *Oryza Sativa* (Rice) Germ Oil. *Oryza Sativa* (Rice) Bran Extract | 0.50 |
|   | Extrapone ® Barley GW | Water (Aqua). Glycerin. *Hordeum Vulgare* Seed Extract | 0.50 |

Example E

Fixative Gel (All Amounts in wt.-%)

| Phase | Component | INCI | Amount |
|---|---|---|---|
| A | Aqua/Water | AQUA | Ad 100 |
|   | Fixate ™* Design Polymer | POLYACRYLATE-32 | 6.0 |
|   | AMP-Ultra ™ PC 2000 | AMINOMETHYL PROPANOL | 0.5 |
|   | SymOcide ® PS | PHENOXYETHANOL, DECYLENE GLYCOL, 1,2-HEXANEDIOL | 1.0 |
| B | Fragrance | PARFUM | 2.0 |
|   | Solubilizer | PEG-40 HYDROGENATED CASTOR OIL, TRIDECETH-9, PROPYLENE GLYCOL, AQUA | 2.0 |
| C | Propylene Glycol | PROPYLENE GLYCOL | 0.5 |
|   | SymHair ® Force 1631 | PENTYLENE GLYCOL, *ISOCHRYSIS GALBANA* EXTRACT | 2.0 |
|   | SymSitive ® | PENTYLENE GLYCOL, 4-T-BUTYLCYCLOHEXANOL | 2.0 |
|   | SymHair ® Restore | GLYCERIN, *TRITICUM VULGARE* (WHEAT), PROTEIN, WATER | 1 |

Example F

Balm for Beard (All Amounts in wt.-%)

| Phase | Component | INCI | Amount |
|---|---|---|---|
| A | Aqua/Water | AQUA | Ad 100 |
|   | Edeta ® BD | DISODIUM EDTA | 0.10 |
|   | SymDiol ® 68 | 1,2-HEXANEDIOL, CAPRYLYL GLYCOL | 0.50 |
|   | SymSave ® H | HYDROXYACETOPHENONE | 0.50 |
| B | Dracorin ® GOC | GLYCERYL OLEATE CITRATE, CAPRYLIC/CAPRIC TRIGLYCERIDE | 2.70 |
|   | SymMollient ® S | CETEARYL NONANOATE | 2.00 |
|   | Phytoconcentrole ® | GLYCINE SOJA OIL, *GOSSYPIUM HERBACEUM* | 4.00 |

| Phase | Component | INCI | Amount |
|---|---|---|---|
| | Fatty Oils Blend | SEED OIL, *MANGIFERA INDICA* SEED BUTTER, *OLEA EUROPAEA* FRUIT OIL, *PERSEA GRATISSIMA* OIL, *PRUNUS AMYGDALUS DULCIS* (SWEET ALMOND) OIL, *THEOBROMA CACAO* SEED BUTTER | |
| | Isodragol ® | TRIISONONANOIN | 3.00 |
| | Isoadipate | DIISOPROPYL ADIPATE | 1.80 |
| | Carbopol ® Ultrez 10 Polymer | CARBOMER | 0.85 |
| | Keltrol ® CG-SFT | XANTHAN GUM | 0.20 |
| C | Sodium Hydroxide 50% solution | AQUA, SODIUM HYDROXIDE | 0.20 |
| D | SymHair ® Force 1631 | PENTYLENE GLYCOL, *ISOCHRYSIS GALBANA* EXTRACT | 4.00 |
| | SymHair ® Restore | GLYCERIN, *TRITICUM VULGARE* (WHEAT), PROTEIN, WATER | 1 |
| | Dragosantol ® | BISABOLOL | 0.2 |
| E | Fragrance | PARFUM | 2.00 |

Example G

Mousse for Hair Volume Improvement (All Amounts in wt.-%)

| Phase | Component | INCI | Amount |
|---|---|---|---|
| A | Aqua/Water | AQUA | Ad 100 |
| | Fixate ™* Design Polymer | POLYACRYLATE-32 | 6.0 |
| | AMP-Ultra ™ PC 2000 | AMINOMETHYL PROPANOL | 0.5 |
| | SymOcide ® PS | PHENOXYETHANOL, DECYLENE GLYCOL, 1,2-HEXANEDIOL | 1.0 |
| B | Fragrance | PARFUM | 2.0 |
| | Solubilizer (660352) | PEG-40 HYDROGENATED CASTOR OIL, TRIDECETH-9, PROPYLENE GLYCOL, AQUA | 2.0 |
| C | Propylene Glycol | PROPYLENE GLYCOL | 0.5 |
| | SymHair ® Force 1631 | PENTYLENE GLYCOL, *ISOCHRYSIS GALBANA* EXTRACT | 2.0 |
| | SymHair Restore | GLYCERIN, *TRITICUM VULGARE* (WHEAT), PROTEIN, WATER | 0.5 |

Example H

Hair Relaxer Cream (All Amounts in wt.-%)

| Phase | Component | INCI | Amount |
|---|---|---|---|
| A | Aqua/Water | AQUA | Ad 100 |
| | Glycerin | GLYCERIN | 5.00 |
| | Calcium Hydroxide | CALCIUM HYDROXIDE | 6.50 |
| B | Alkonat ® 1618 C30 | CETEARYL ALCOHOL | 12.00 |
| | Eumulgin ® B2 | CETEARETH-20 | 2.00 |
| | Mineral Oil | PARAFFINUM LIQUIDUM | 15.00 |
| C | Kathon ® CG | METHYLCHLOROISOTHIAZOLINONE, METHYLISOTHIAZOLINONE | 0.05 |
| | SymHair ® Restore | GLYCERIN, *TRITICUM VULGARE* (WHEAT), PROTEIN, WATER | 1.00 |

Example I

Hair Coloration (All Amounts in wt.-%)

| Phase | Component | INCI | Amount |
|---|---|---|---|
| A | Oxowax | CETYL ALCOHOL, OLEYL ALCOHOL, CETEARYL ALCOHOL, STEARIC ACID | 21.0 |
| A | Brij™ CS25-PA-(RB) | CETEARETH-25 | 4.0 |
| A | Elfacos ® EA-75 | LAURETH-8 | 10.0 |
| A | Lanette ® E | SODIUM CETEARYL SULFATE | 1.0 |
| A | Covaquat 16 | POLYQUATERNIUM-6, AQUA | 4.0 |
| A | Aqua/Water | AQUA | 49.3 |
| B | Ammonia 20% Sol. | AMMONIA | 10.2 |
| C | SymHair ® Shape | CETEARYL NONANOATE, *TRITICUM VULGARE* BRAN EXTRACT, ETHYLHEXYL ISONONANOATE, LINOLEIC ACID, *CAMELLIA OLEIFERA* SEED OIL | 0.5 |
| C | SymHair ® Restore | GLYCERIN, *TRITICUM VULGARE* (WHEAT), PROTEIN, WATER | 1.00 |
| C | SymSitive | PENTYLENE GLYCOL, 4-T-BUTYLCYCLOHEXANOL | 6.0 |

Skin Care Formulations

1=Skin soothing Balm
2=Tinted Anti-Aging Balm, SPF 15
3=After-sun skin hydrating spray O/W
4=Night Cream W/O
5=Face clearing gel
6=After-Shave Hydrogel
7=Antiperspirant pump spray
8=Skin lightening day care fluid O/W
9=Barrier restoring cream O/W
10=Sun protecting lotion SPF 24 (UVA/UVB balance)

| Ingredient | 1 | 2 | 3 | 4 | 5 | 6 | 7 | 8 | 9 | 10 |
|---|---|---|---|---|---|---|---|---|---|---|
| SymHair Restore Glycerin, *Triticum Vulgare* (Wheat) Protein, Water | 1 | 0.5 | 2 | 1 | 2 | 1.5 | 0.2 | 0.5 | 2 | 1 |
| Actipone ® *Laminaria Saccharina* Glycerin, Water (Aqua), *Laminaria Saccharina* Extract | 1 | 0.5 | 2 | 1 | 2 | 1.5 | 0.2 | 0.5 | 2 | 1 |
| Allantoin Allantoin | 0.1 | | | | | 0.1 | | | | |
| *Aloe Vera* Gel Conc. 10:1 *Aloe Barbadensis*(*Aloe*) Leaf Juice | | | | | | 1 | | | | |
| Aluminium Stearate Aluminium Stearate | | | | 1.2 | | | | | | |
| Beta-Arbutin Arbutin | | | | | | | | 1 | | |
| Avocado Oil *Persea Gratissima* (Avocado) Oil | | | | 3 | | | | | | |
| Betulin 90% Betulin | | | | | | | | | 0.1 | |
| Biotive L-Arginin Arginine | | | 0.6 | | | | | | | 0.5 |
| Biotive Troxerutin Troxerutin | | | 0.5 | | | | | | | 0.5 |
| (—)-alpha-Bisabolol Bisabolol | | | | | | | | | | 0.1 |
| Carbopol Aqua SF-1 Polymer Acrylates Copolymer | | | | | 5 | | | | | |
| Carbopol ® Ultrez-10 Carbomer | | | 0.2 | | | | 0.4 | 0.2 | | |
| CeramideBIO ® Cetylhydroxyproline Palmitamide | | | | | | | | | 0.5 | |
| Citric acid 10% in water | | | | | | 0.2 | | | | |
| Covi-Ox ® T-70 Tocopherol | | | | 0.1 | | | | | | |
| Cutina ® PES Pentaerythrityl Distearate | | 2 | | | | | | | | |
| D-Panthenol Panthenol | 1 | | 1 | | | 0.5 | | | | |
| Dehyton K Cocamidopropyl Betaine | | | | | | 8 | | | | |
| Dermacryl ® AQF Acrylates Copolymer | | | | | | | | | | 2 |
| Dow Corning 200(100cs) Silicone Fluid Dimethicone | 2 | 2 | | | | | | 0.5 | 0.5 | |
| Dow Corning 246 Fluid Cyclohexasiloxane, | | | | 2 | | | | | | 3 |

-continued

| Ingredient | 1 | 2 | 3 | 4 | 5 | 6 | 7 | 8 | 9 | 10 |
|---|---|---|---|---|---|---|---|---|---|---|
| Cyclopentasiloxane | | | | | | | | | | |
| Dracorin ® CE | | | | | | | | | 1.5 | |
| Glyceryl Stearate Citrate | | | | | | | | | | |
| Dracorin ® GMS | | | | | | | | | 2 | |
| Glyceryl Stearate | | | | | | | | | | |
| Dracorin ® GOC | | | 2 | | | | | | | |
| Glyceryl Oleate Citrate, Caprylic/Capric Triglyceride | | | | | | | | | | |
| Dragocalm ® | 1 | | | | | | | | | |
| Water (Aqua), Glycerin, *Avena Sativa* (Oat) Kernel Extract | | | | | | | | | | |
| Dragocid ® Liquid | | | | | | | | 0.8 | | |
| Phenoxyethanol, Methylparaben, Ethylparaben, Butylparaben, Propylparaben, Isobutylparaben | | | | | | | | | | |
| Dragosan ® W/O P | | | | 8 | | | | | | |
| Sorbitan Isostearate, Hydrogenated Castor Oil, Ceresin, Beeswax (*Cera Alba*) | | | | | | | | | | |
| Dragosantol ® 100 | | | | | 0.2 | | | | | |
| Bisabolol | | | | | | | | | | |
| Dragosine ® | | 0.2 | | | | | | | | |
| Carnosine | | | | | | | | | | |
| Dragoxat ® 89 | | 5 | | 7 | | | | | 2 | 2 |
| Ethylhexyl Isononanoate | | | | | | | | | | |
| Dinatrium EDTA | 0.1 | 0.1 | | | | | | 0.1 | | 0.1 |
| Emulsiphos ® | | 2 | | | | | | 1.5 | 2 | 2 |
| Potassium Cetyl Phosphate, Hydrogenated Palm Glycerides | | | | | | | | | | |
| Ethanol | | | 5 | | | 8 | | | | |
| Extrapone ® Aloe vera | | | | | | 2 | | | | |
| Water (Aqua), *Aloe Barbadensis*, Propylene Glycol, Alcohol | | | | | | | | | | |
| Extrapone ® Witch Hazel | 1 | | | | | | | | | |
| Propylene Glycol, *Hamamelis Virginiana* (Witch Hazel) Water, Water (Aqua), *Hamamelis Virginiana* (Witch Hazel) Extract | | | | | | | | | | |
| Extrapone ® Seaweed Water | | | | | | 0.5 | | | | |
| (Aqua), Butylene Glycol, *Fucus Vesiculosus* Extract | | | | | | | | | | |
| Farnesol DT | | | | | | | 0.2 | | | |
| Phenoxyethanol, Farnesol, Bisabolol | | | | | | | | | | |
| Food Color Brown | | 2 | | | | | | | | |
| E172 + E171 Powder | | | | | | | | | | |
| Frescolat ® MGA | | | 0.1 | | | | | | | |
| Menthone Glycerin Acetal | | | | | | | | | | |
| Frescolat ® ML | | | 0.5 | | | 0.3 | | | | |
| Menthyl Lactate | | | | | | | | | | |
| Frescolat ® X-Cool | | | | | | | | | 0.2 | |
| Menthyl Ethylamido Oxalate | | | | | | | | | | |
| Givobio ® GZN | | | | | | | | | 0.5 | |
| Zinc Gluconate | | | | | | | | | | |
| Glycerin | 1.5 | | 4 | 3 | | | | 3.5 | 3 | 3 |
| Hydrolite ® 5 | 3 | | 5 | | 2 | 5 | 5 | | | 2 |
| Pentylene Glycol | | | | | | | | | | |
| Hydroviton-24 ® | | | | 1 | | | | | | |
| Water (Aqua), Pentylene Glycol, Glycerin, Lactic Acid, Sodium Lactate, Serine, Urea, Sorbitol, Sodium Chloride, Allantoin | | | | | | | | | | |
| Hydroviton ® Plus 2290 | | | | | | | | 1 | | 2 |
| Water (Aqua), Pentylene Glycol, Glycerin, Fructose, Urea, Citric acid, Sodium Hydroxide, Maltose, Sodium PCA, Sodium Chloride, Sodium Lactate, Trehalose, Allantoin, Sodium Hyaluronate, Glucose | | | | | | | | | | |
| Isoadipate | | | | | | | | 2 | | |
| Diisopropyl Adipate | | | | | | | | | | |
| Isodragol ® | 1 | | | | | | | | 3 | 2 |
| Triisononanoin | | | | | | | | | | |
| Jojoba Oil | | | | 2 | | | | | | |
| *Simmondsia Chinensis* (Jojoba) Seed Oil | | | | | | | | | | |

-continued

| Ingredient | 1 | 2 | 3 | 4 | 5 | 6 | 7 | 8 | 9 | 10 |
|---|---|---|---|---|---|---|---|---|---|---|
| Kaliumsorbat | | | 0.1 | | | | | | | |
| Keltrol ® CG-RD Xanthan Gum | | 0.2 | | | | | | 0.2 | | 0.4 |
| Kojic acid | | | | | | | | | | |
| Kojic acid | | | | | | | | 0.5 | | |
| Lanette ® 16 Cetyl Alcohol | | | | | | | | 1.5 | | 1 |
| Lanette ® O Cetearyl Alcohol | | | | | | | | | 2 | 0.5 |
| Lara Care ® A-200 Galactoarabinan | | | | | | | | | | 0.3 |
| Locron ® L Aluminium Chlorohydrate | | | | | | | 16 | | | |
| Magnesium sulfate | | | | 0.7 | | | | | | |
| Mineral oil | | | | 8 | | | | | | |
| Sodium ascorbylphosphate | | | | | | | | 1 | | |
| Natriumchlorid Sodium hydroxide 10% in water | 1 | | | | 2 | 0.7 | | 0.2 | 0.3 | |
| Neo Heliopan ® 303 Octocrylene | | 4 | | | | | | | | 10 |
| Neo Heliopan ® 357 Butylmethoxydibenzoyl-methane | | 2 | | | | | | 2 | | 3 |
| Neo Heliopan ® AP, 15% Lösung, neutralized with L-Arginin, Aqua, Disodium Phenyl Dibenzimidazole Tetrasulfonate, Arginin | | 6.7 | | | | | | | | 6.7 |
| Neo Heliopan ® AV Ethylhexyl Methoxycinnamate | | | | | | | | 7.5 | | |
| Neo Heliopan ® BB Benzophenone-3 | | | | | | | | 3 | | |
| Neo Heliopan ® E 1000 Isoamyl p.Methoxycinnamate | | | | | | | | | | 1 |
| Neo Heliopan ® HMS Homosalate | | | | | | | | 10 | | 5 |
| Neo Heliopan ® OS Ethylhexyl Salicylate | | 3 | | | | | | 5 | | |
| Neo Heliopan ® Hydro, 20% Lösung, neutralized with Biotive Arginine; Aqua, Phenylbenzimidazole, Sulphonic Acid, Arginin | | 10 | | | | | | | | 10 |
| Neo-PCL Water Soluble N Trideceth-9, PEG-5 Ethylhexanoate, Water (Aqua) | | | | | | 1 | 2 | | | |
| Neutral oil Caprylic/Capric Triglyceride | | | 5 | | | | | | 10 | |
| Niacinamide | | | | | 1 | | | | | |
| Ozokerite Wax 2389 Ozokerite | | | | 2 | | | | | | |
| Parfum | 0.05 | 0.3 | 0.25 | 0.3 | | 0.1 | 0.7 | 0.3 | 0.1 | 0.2 |
| Parfum PCL-Liquid 100 Cetearyl Ethylhexanoate | 3 | 2 | 4 | 5 | | | | | | |
| PCL-Solid Stearyl Heptanoate, Stearyl Caprylate | 1 | | 0.5 | | | | | | | |
| Pemulen ® TR-2 Acrylates/C10-30 Alkyl Acrylate Crosspolymer | 0.6 | | 0.25 | | | | | | | |
| Phenethylalcohol | | | | | 0.2 | | | | | |
| Phenoxyethanol | | | | | | | | | | 0.2 |
| Phytoconcentrole ® Shea Butter, Glycine Soja (Soybean) Oil, *Butyrospermum Parkii* (Shea Butter) | 1 | | | | | | | | | |
| Propylene glycol-1,2 Propylene Glycol | | | | | | 5 | 3 | | | |
| Silcare Silicone 41M65 Stearyl Dimethicone | | | | | | | | | | 1 |
| Solubilizer PEG-40 Hydrogenated Castor Oil, Tridecth-9, Propylene Glycol, Water (Aqua) | | | | | | | | 3 | | |
| Sulfetal LA Ammonium Lauryl Sulfate | | | | | | | 12 | | | |

-continued

| Ingredient | 1 | 2 | 3 | 4 | 5 | 6 | 7 | 8 | 9 | 10 |
|---|---|---|---|---|---|---|---|---|---|---|
| SymCalmin® Butylene Glycol, Pentylene Glycol, Hydroxyphenyl Propamidobenzoic Acid | 1 | | | | | | | | 0.1 | |
| SymClariol® Decylene Glycol | | 0.5 | | | 1 | | | 0.3 | | |
| SymDecanox HA Caprylic/Capric Triglyceride, Hydroxymethoxyphenyl Decanone | | | 2 | | | | | | | |
| SymDeo® B125 2-Methyl 5-Cyclohexylpentanol | | | | | | | 0.2 | | | |
| SymDeo® MPP Dimethyl Phenyl 2-Butanol | | | | | | | 0.5 | | | |
| Symdiol® 68 1.2-Hexanediol, Caprylyl Glycol | 1 | 0.5 | | | | | | | | 0.3 |
| SymFinity® 1298 *Echinacea Purpurea* Extract | | | | 0.05 | | | | | | |
| SymGlucan® Water (Aqua), Glycerin, Beta-Glucan | 1 | | 5 | | | | | | | 2 |
| SymHelios® 1031 Benzylidene Dimethoxydimethylindanone | | 0.5 | | | | | | | | |
| SymLift Water, trehalose, glycerin, pentylene glycol, beta-glucan, *hordeum vulgare* seed extract, sodium hyaluronate, 1,2-Hexanediol, caprylyl glycol, sodium benzoate, maltodextrine | | 2 | | | | | | | | |
| SymMatrix Maltodextrin, *Rubus Fruticosus* (Blackberry) Leaf Extract | | 0.1 | 0.3 | | | | | | | |
| SymMollient® W/S Trideceth-9, PEG-5 Isononanoate, Water (Aqua) | | | | | 2 | | | | | |
| SymOcide® C o-Cymen-5-ol | | | | | | 0.1 | | | | |
| SymOcide® PS Phenoxyethanol, Decylene Glycol, 1,2-Hexanediol | | | | | | | | | 0.8 | |
| SymOcide® PT Phenoxyethanol, Tropolone | | | | 0.8 | | | | | | |
| SymPeptide® 225 Glycerin, Water (Aqua), Myristoyl Pentapeptide-11 | | | | 1 | | | | | | |
| SymRelief® 100 Bisabolol, *Zingiber Officinale* (Ginger) Root Extract | | | | | | | 0.2 | | | |
| SymRelief S Bisabolol, Hydroxymethoxyphenyl Decanone | | | | | | | | | 0.1 | |
| SymRepair® 100 Hexyldecanol, Bisabolol, Cetylhydroxyproline Palmitamide, Stearic Acid, *Brassica Campestris* (Rapeseed) Sterols | | 1 | 3 | | | | | | | |
| SymSave® H Hydoxyacetophenone | | 0.5 | | | 0.8 | 0.5 | | | | 0.5 |
| SymSol® PF-3 Water (Aqua), Pentylene Glycol, Sodium Lauryl Sulfoacetate, Sodium Oleoyl Sarcosinate, Sodium Chloride, Disodium Sulfoacetate, Sodium Oleate, Sodium Sulfate | | | | | | 1.3 | | | | |
| SymSitive® 1609 Pentylene Glycol, 4-t-Butylcyclohexanol | | | 0.5 | | | | | 0.5 | | |
| SymVital® AgeRepair 3040 *Zingiber Officinale* (Ginger) Root Extract | | | 0.1 | | | | | | | |
| SymWhite® 377 Phenylethyl Resorcinol | | | | | | | | 0.5 | | |
| Tamasterol® Phytosterols | | | | | | | | | 0.3 | |
| Tapioca Pure Tapioca Starch | | | | | | | | | | 5 |

| Ingredient | 1 | 2 | 3 | 4 | 5 | 6 | 7 | 8 | 9 | 10 |
|---|---|---|---|---|---|---|---|---|---|---|
| Tegosoft ® PC 31 | | | | | | | | | 0.3 | |
| Polyglyceryl-3 Caprate | | | | | | | | | | |
| Triethanolamine | | | 0.3 | | | | | | | |
| Vitamin A Palmitate | | | | 0.1 | | | | | | |
| Retinyl Palmitate | | | | | | | | | | |
| Vitamin E Acetate | | 0.5 | | 0.2 | | | | | 0.3 | 0.5 |
| Tocopheryl Acetate | | | | | | | | | | |
| Zetesol LA-2 | | | | | 26 | | | | | |
| Ammonium Laureth Sulfate | | | | | | | | | | |
| Water | | | | | Ad 100 | | | | | |

What is claimed is:

1. A mixture comprising:
   (a) about 9 to about 11 wt.-% protein extract obtained from cereal gluten extracted by aqueous ethanol, said extract having a content of at least 50 wt.-% proteins having a molecular weight of at least 22 kDa;
   (b) about 0.03 to about 0.1 wt.-% of at least one organic acid; and
   (c) at least one cosmetically acceptable carrier,
   wherein said protein extract (component a) is obtained by a method comprising the following steps
   (i) extracting dried cereal gluten with an extraction medium comprising dilute alkanol to obtain a liquid extract comprising proteins, wherein the protein fraction of the extract consists essentially of prolamines;
   (ii) removing solid residue from the resulting liquid extract to produce a liquid phase;
   (iii) treating said liquid phase with a polyhydric alcohol selected from the group consisting of glycerol, a short chain alkanediol and mixtures thereof; and
   (iv) concentrating the resultant treated liquid phase under reduced pressure until the resultant liquid concentrate has an alkanol content of less than 5 percent by weight,
   wherein amount of said protein extract, organic acid, and carrier, together with any further additive, total 100 wt.-%,
   ratio of protein extract (a) to organic acid (b) is from about 1:0.01 to about 1:0.03, and
   said organic acid (b) is selected from the group consisting of citric acid, lactic acid, isocitric acid, malic acid, glycolic acid, mandelic acid, tartronic acid, and mixtures thereof.

2. The mixture of claim 1, wherein said carrier (component c) is selected from the group consisting of water, $C_1$-$C_4$ aliphatic alcohols, polyols, and mixtures thereof.

3. The mixture of claim 1, further comprising at least one hair conditioning agent.

4. The mixture of claim 3, wherein said hair conditioning agent is selected from the group consisting of quaternary surfactants, cationic polymers, silicones, and mixtures thereof.

5. A skin care composition comprising about 0.1 to about 10% by weight of the mixture of claim 1.

6. A method for improving water resistance of skin care and particularly sun care compositions comprising primary and/or secondary sun protection filters, comprising adding the mixture of claim 1.

7. A hair care composition comprising about 0.1 to about 10% by weight of the mixture of claim 1.

8. The composition of claim 7 representing a two-in-one hair shampoo.

9. A method for
   improving break resistance, volume, combability and lustre, and/or
   reducing split ends, fatigue and swelling of damaged, and particularly undamaged human hair, comprising applying the mixture of claim 1 to human hair.

10. The method of claim 9, wherein the mixture is applied to damaged or undamaged human hair.

11. A method for improving break resistance, volume, combability and lustre, and/or reducing split ends, fatigue and swelling of damaged, and particularly undamaged human hair, comprising
   applying the composition of claim 7 to human hair.

12. The method according to claim 11, comprising the step of
   simultaneously improving break resistance, volume, combability and lustre, and reducing split ends, fatigue and swelling of damaged, and particularly undamaged human hair.

13. The method according to claim 9, comprising the step of
   simultaneously improving break resistance, volume, combability and lustre, and reducing split ends, fatigue and swelling of damaged, and particularly undamaged human hair.

* * * * *